United States Patent
Xiao et al.

(10) Patent No.: US 10,948,504 B2
(45) Date of Patent: *Mar. 16, 2021

(54) MATERIAL AND METHOD FOR COLORIMETRIC DETECTION OF SMALL-MOLECULE TARGETS

(71) Applicants: Yi Xiao, Miami, FL (US); Yingping Luo, Miami, FL (US); Haixiang Yu, Miami, FL (US)

(72) Inventors: Yi Xiao, Miami, FL (US); Yingping Luo, Miami, FL (US); Haixiang Yu, Miami, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/902,717

(22) Filed: Jun. 16, 2020

(65) Prior Publication Data

US 2020/0355708 A1    Nov. 12, 2020

Related U.S. Application Data

(63) Continuation of application No. 16/179,336, filed on Nov. 2, 2018, now Pat. No. 10,725,058.

(51) Int. Cl.
| | | |
|---|---|---|
| *C12N 15/115* | (2010.01) | |
| *C12Q 1/6883* | (2018.01) | |
| *G01N 33/94* | (2006.01) | |
| *G01N 33/52* | (2006.01) | |

(52) U.S. Cl.
CPC ......... *G01N 33/9486* (2013.01); *G01N 33/52* (2013.01)

(58) Field of Classification Search
CPC .. C12N 15/10; C12N 15/115; C12N 2310/16; C12N 2330/31; C12Q 1/6883
USPC .... 435/6.1, 91.1, 91.31, 455, 458; 536/23.1, 536/24.5
See application file for complete search history.

(56) References Cited

U.S. PATENT DOCUMENTS

| 9,804,178 B2 | 10/2017 | Roncancio et al. |
| 10,550,395 B2 | 2/2020 | Xiao et al. |
| 10,725,058 B2 * | 7/2020 | Xiao ................. G01N 33/9486 |

OTHER PUBLICATIONS

Gerasimova, Yulia V., et al., "Enzyme-assisted target recycling (EATR) for nucleic acid detection." Chem. Soc. Rev., 2014, 43, 6405-6438.
Wu, Di, et al., "A label-free electrochemical DNA sensor based on exonuclease III-aided target recycling strategy for sequence-specific detection of femtomolar DNA." Biosensors and Bioelectronics, 2011, 28: 232-238.
Wu, Shuo, et al., "Amplified Single Base-Pair Mismatch Detection via Aggregation of Exonuclease-Sheared Gold Nanoparticles." Analytical Chemistry, 2014, 86: 3461-3467.
Yu, Haixiang, et al., "A cooperative-binding split aptamer assay for rapid, specific and ultra-sensitive fluorescence letection of cocaine in saliva." Chemical Science, 2017, 8: 131-141.
Yu, Haixiang, et al., "Sensitive Detection of Small-Molecule Targets Using Cooperative Binding Split Aptamers and Enzyme-Assisted Target Recycling." Analytical Chemistry, 2018, 90: 1748-1758.
Zuo, Xiaolei, et al., "Sensitive and Selective Amplified Fluorescence DNA Detection Based on Exonuclease III-Aided Target Recycling." J. Am. Chem. Soc., 2010, 132: 1816-1818.

* cited by examiner

*Primary Examiner* — Jane J Zara
(74) *Attorney, Agent, or Firm* — Saliwanchik, Lloyd & Eisenschenk

(57) ABSTRACT

The subject invention provides methods, assays, and products for visual detection of small-molecule targets in a sample in both clinical and field settings within minutes. The subject invention is based on an aptamer sensor that reports the presence of small-molecule target via a sensitive colorimetric signal for naked-eye detection. The aptamer sensor is a CBSAzyme-based sensor having both target-mediated cooperative behavior of the CBSA and peroxidase-mimicking catalytic activity of DNAzyme. The subject invention also provides methods of using the CBSAzyme-based sensor.

20 Claims, 20 Drawing Sheets
(20 of 20 Drawing Sheet(s) Filed in Color)
Specification includes a Sequence Listing.

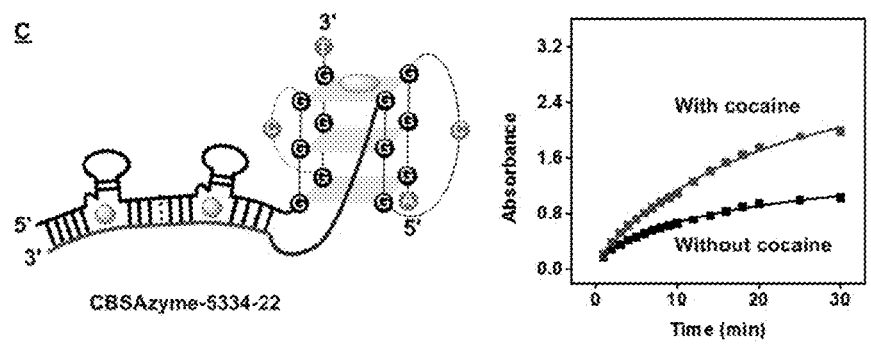
FIG. 6C
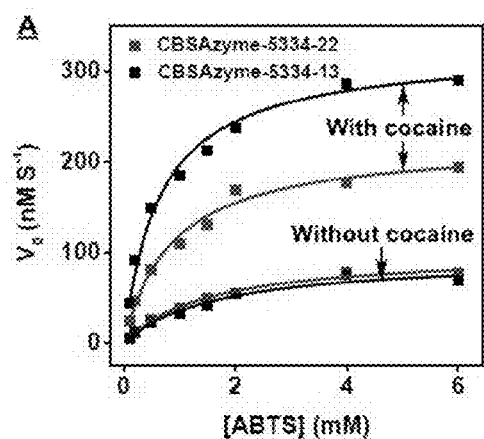
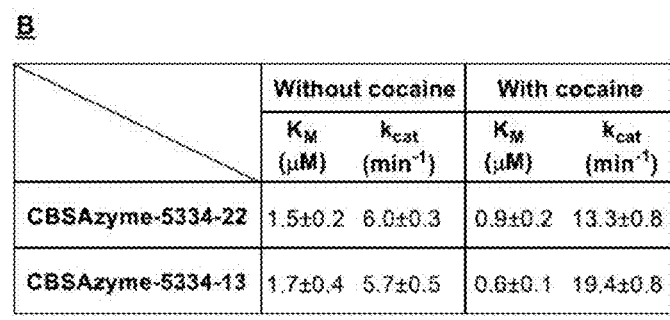
FIG. 7A
FIG. 7B

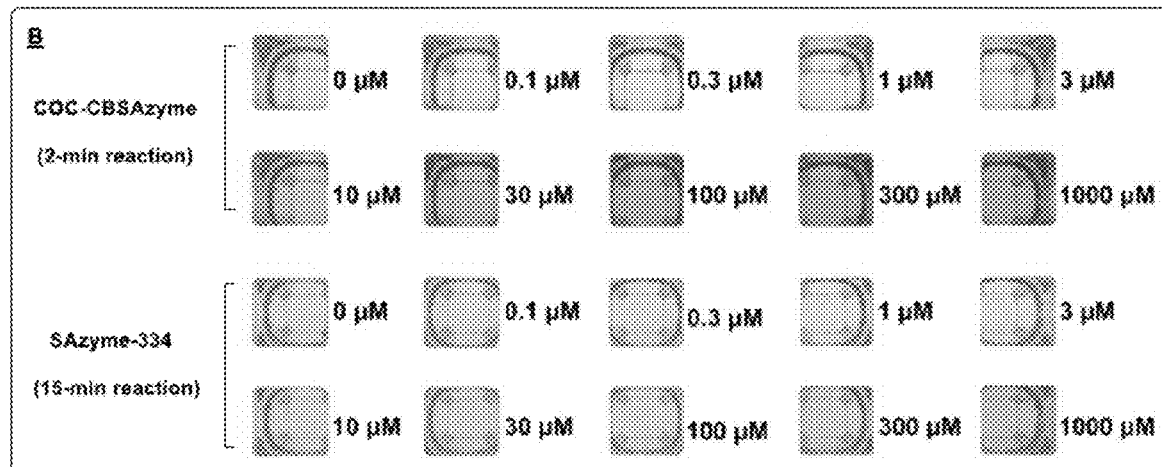
FIG.16B
FIG. 17A
FIG.17B
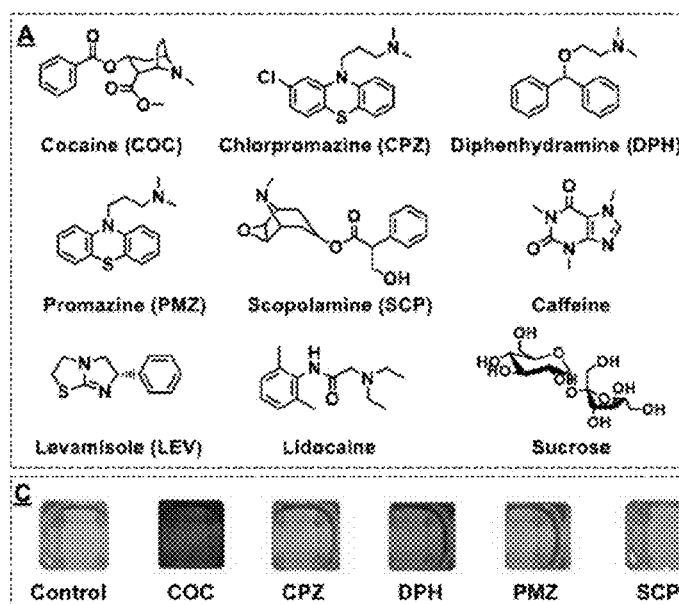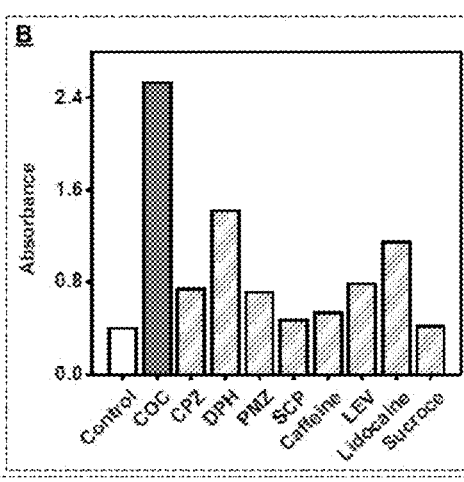
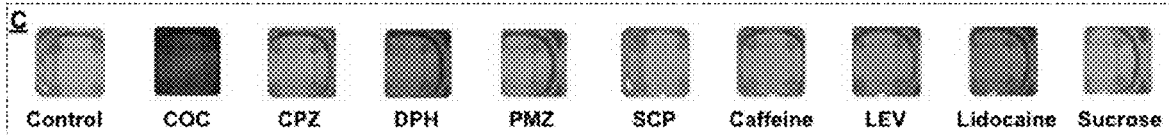
FIG.17C

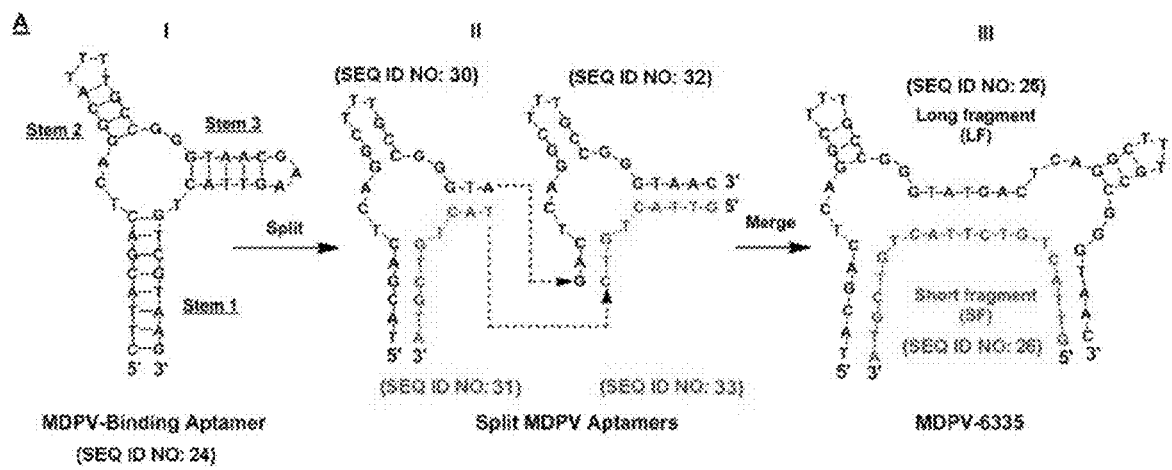
FIG. 18A
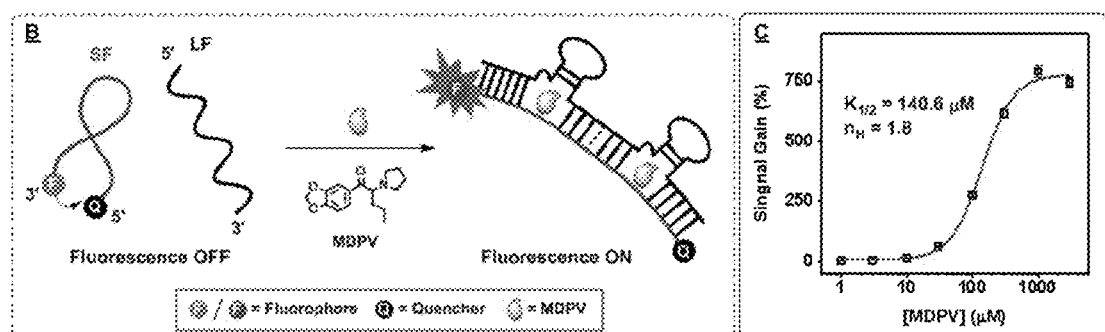
FIG. 18B
FIG. 18C

FIG. 19A   FIG.19B

FIG. 21A
FIG. 21B
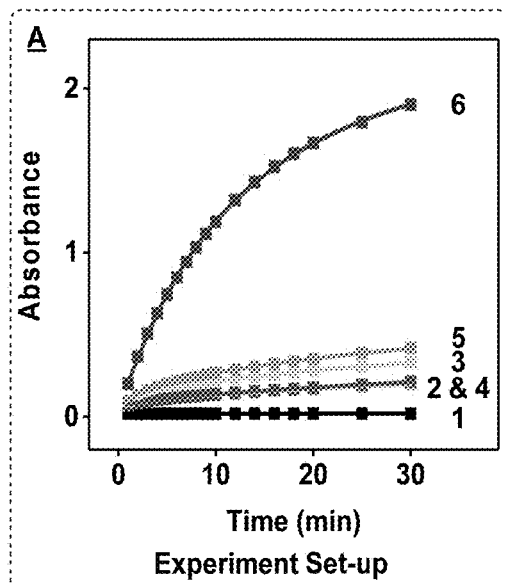
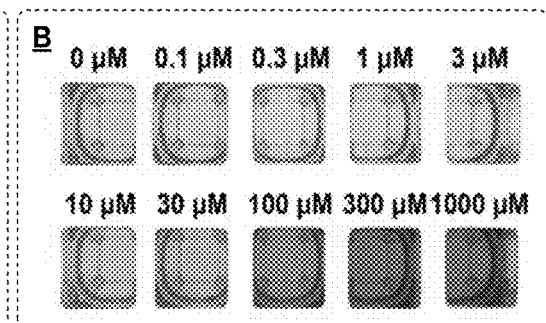
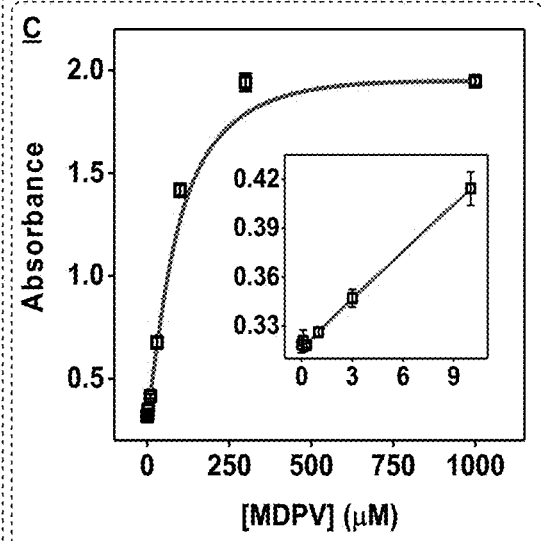
FIG. 21C

SEQUENCE LISTING

<160> NUMBER OF SEQ ID NOS: 45

<210> SEQ ID NO 1
<211> LENGTH: 31
<212> TYPE: DNA
<213> ORGANISM: Artificial sequence
<220> FEATURE:
<223> OTHER INFORMATION: oligonucleotide
<220> FEATURE:
<221> NAME/KEY: misc_feature
<222> LOCATION: (22)..(23)
<223> OTHER INFORMATION: nn = a, c, t, aa, ac, at, cc, ca, ct, ta, tc,
      or tt, or the nucleotide may be absent
<220> FEATURE:
<221> NAME/KEY: misc_feature
<222> LOCATION: (26)..(27)
<223> OTHER INFORMATION: nn = a, c, t, aa, ac, at, cc, ca, ct, ta, tc,
      or tt, or the nucleotide may be absent

<400> SEQUENCE: 1
agtaacaaca atcaaaatat gnnggnnggg t                                    31

<210> SEQ ID NO 2
<211> LENGTH: 29
<212> TYPE: DNA
<213> ORGANISM: Artificial sequence
<220> FEATURE:
<223> OTHER INFORMATION: oligonucleotide

<400> SEQUENCE: 2
agtaacaaca atcaaaatat gtggagggt                                       29

<210> SEQ ID NO 3
<211> LENGTH: 28
<212> TYPE: DNA
<213> ORGANISM: Artificial sequence
<220> FEATURE:
<223> OTHER INFORMATION: oligonucleotide

<400> SEQUENCE: 3
agtaacaaca atcaaaatat gggagggt                                        28

<210> SEQ ID NO 4
<211> LENGTH: 28
<212> TYPE: DNA
<213> ORGANISM: Artificial sequence
<220> FEATURE:
<223> OTHER INFORMATION: oligonucleotide

<400> SEQUENCE: 4
agtaacaaca atcaaaatat gggcgggt                                        28

<210> SEQ ID NO 5
<211> LENGTH: 29
<212> TYPE: DNA
<213> ORGANISM: Artificial sequence
<220> FEATURE:
<223> OTHER INFORMATION: oligonucleotide
<220> FEATURE:
<221> NAME/KEY: misc_feature
<222> LOCATION: (5)..(6)
<223> OTHER INFORMATION: nn = a, c, t, aa, ac, at, cc, ca, ct, ta, tc,
      or tt, or the nucleotide may be absent

<400> SEQUENCE: 5
agggnnggga aatttgatt gttgttact                                        29

<210> SEQ ID NO 6

```
<211> LENGTH: 29
<212> TYPE: DNA
<213> ORGANISM: Artificial sequence
<220> FEATURE:
<223> OTHER INFORMATION: oligonucleotide

<400> SEQUENCE: 6
agggacggga aattttgatt gttgttact                              29

<210> SEQ ID NO 7
<211> LENGTH: 28
<212> TYPE: DNA
<213> ORGANISM: Artificial sequence
<220> FEATURE:
<223> OTHER INFORMATION: oligonucleotide

<400> SEQUENCE: 7
agggcgggaa attttgattg ttgttact                               28

<210> SEQ ID NO 8
<211> LENGTH: 41
<212> TYPE: DNA
<213> ORGANISM: Artificial sequence
<220> FEATURE:
<223> OTHER INFORMATION: oligonucleotide

<400> SEQUENCE: 8
ctccttcaac gaagtgggtc tccttcaacg aagtgggtct c                41

<210> SEQ ID NO 9
<211> LENGTH: 19
<212> TYPE: DNA
<213> ORGANISM: Artificial sequence
<220> FEATURE:
<223> OTHER INFORMATION: oligonucleotide

<400> SEQUENCE: 9
gagacaaggt gacaaggag                                         19

<210> SEQ ID NO 10
<211> LENGTH: 51
<212> TYPE: DNA
<213> ORGANISM: Artificial sequence
<220> FEATURE:
<223> OTHER INFORMATION: oligonucleotide

<400> SEQUENCE: 10
ctccttcaac gaagtgggtc tccttcaacg aagtgggtct catgggcggg t     51

<210> SEQ ID NO 11
<211> LENGTH: 29
<212> TYPE: DNA
<213> ORGANISM: Artificial sequence
<220> FEATURE:
<223> OTHER INFORMATION: oligonucleotide

<400> SEQUENCE: 11
agggcgggaa gagacaaggt gacaaggag                              29

<210> SEQ ID NO 12
<211> LENGTH: 50
<212> TYPE: DNA
<213> ORGANISM: Artificial sequence
<220> FEATURE:
<223> OTHER INFORMATION: oligonucleotide

<400> SEQUENCE: 12
```
ctccttcaac gaagtgggtc tccttcaacg aagtgggtct atgggcgggt                50

<210> SEQ ID NO 13
<211> LENGTH: 28
<212> TYPE: DNA
<213> ORGANISM: Artificial sequence
<220> FEATURE:
<223> OTHER INFORMATION: oligonucleotide

<400> SEQUENCE: 13
agggcgggaa agacaaggtg acaaggag                                        28

<210> SEQ ID NO 14
<211> LENGTH: 49
<212> TYPE: DNA
<213> ORGANISM: Artificial sequence
<220> FEATURE:
<223> OTHER INFORMATION: oligonucleotide

<400> SEQUENCE: 14
ctccttcaac gaagtgggtc tccttcaacg aagtgggtca tgggcgggt                 49

<210> SEQ ID NO 15
<211> LENGTH: 27
<212> TYPE: DNA
<213> ORGANISM: Artificial sequence
<220> FEATURE:
<223> OTHER INFORMATION: oligonucleotide

<400> SEQUENCE: 15
agggcgggaa gacaaggtga caaggag                                         27

<210> SEQ ID NO 16
<211> LENGTH: 18
<212> TYPE: DNA
<213> ORGANISM: Artificial sequence
<220> FEATURE:
<223> OTHER INFORMATION: oligonucleotide

<400> SEQUENCE: 16
agacaaggtg acaaggag                                                   18

<210> SEQ ID NO 17
<211> LENGTH: 39
<212> TYPE: DNA
<213> ORGANISM: Artificial sequence
<220> FEATURE:
<223> OTHER INFORMATION: oligonucleotide

<400> SEQUENCE: 17
ctccttcaac gaagtgggtc tccttcaacg aagtgggtc                            39

<210> SEQ ID NO 18
<211> LENGTH: 45
<212> TYPE: DNA
<213> ORGANISM: Artificial sequence
<220> FEATURE:
<223> OTHER INFORMATION: oligonucleotide

<400> SEQUENCE: 18
ctccttcaac gaagtgggtc tccttcaacg aagtgggtct atggg                     45

<210> SEQ ID NO 19
<211> LENGTH: 32
<212> TYPE: DNA

<213> ORGANISM: Artificial sequence
<220> FEATURE:
<223> OTHER INFORMATION: oligonucleotide

<400> SEQUENCE: 19
gggtagggcg ggaaagacaa ggtgacaagg ag                          32

<210> SEQ ID NO 20
<211> LENGTH: 44
<212> TYPE: DNA
<213> ORGANISM: Artificial sequence
<220> FEATURE:
<223> OTHER INFORMATION: oligonucleotide

<400> SEQUENCE: 20
ctccttcaac gaagtgggtc tccttcaacg aagtgggtct aggg             44

<210> SEQ ID NO 21
<211> LENGTH: 31
<212> TYPE: DNA
<213> ORGANISM: Artificial sequence
<220> FEATURE:
<223> OTHER INFORMATION: oligonucleotide

<400> SEQUENCE: 21
gggtagggcg ggaagacaag gtgacaagga g                           31

<210> SEQ ID NO 22
<211> LENGTH: 27
<212> TYPE: DNA
<213> ORGANISM: Artificial sequence
<220> FEATURE:
<223> OTHER INFORMATION: oligonucleotide

<400> SEQUENCE: 22
gtctccttca acgaagtggg tctaggg                                27

<210> SEQ ID NO 23
<211> LENGTH: 26
<212> TYPE: DNA
<213> ORGANISM: Artificial sequence
<220> FEATURE:
<223> OTHER INFORMATION: oligonucleotide

<400> SEQUENCE: 23
gggtagggcg ggaaagacaa ggtgac                                 26

<210> SEQ ID NO 24
<211> LENGTH: 46
<212> TYPE: DNA
<213> ORGANISM: Artificial sequence
<220> FEATURE:
<223> OTHER INFORMATION: oligonucleotide

<400> SEQUENCE: 24
cttacgactc aggcattttg ccgggtaacg aagttactgt cgtaag           46

<210> SEQ ID NO 25
<211> LENGTH: 46
<212> TYPE: DNA
<213> ORGANISM: Artificial sequence
<220> FEATURE:
<223> OTHER INFORMATION: oligonucleotide

<400> SEQUENCE: 25
tacgactcag gctttgccgg gtatgactca ggctttgccg ggtaac           46

<210> SEQ ID NO 26
<211> LENGTH: 20
<212> TYPE: DNA
<213> ORGANISM: Artificial sequence
<220> FEATURE:
<223> OTHER INFORMATION: oligonucleotide

<400> SEQUENCE: 26
gttactgtct tactgtcgta                                           20

<210> SEQ ID NO 27
<211> LENGTH: 20
<212> TYPE: DNA
<213> ORGANISM: Artificial sequence
<220> FEATURE:
<223> OTHER INFORMATION: oligonucleotide
<220> FEATURE:
<221> NAME/KEY: misc_feature
<222> LOCATION: (1)..(1)
<223> OTHER INFORMATION: Iowa Black RQ quencher modification
<220> FEATURE:
<221> NAME/KEY: misc_feature
<222> LOCATION: (20)..(20)
<223> OTHER INFORMATION: Cy5 fluorophore modification

<400> SEQUENCE: 27
gttactgtct tactgtcgta                                           20

<210> SEQ ID NO 28
<211> LENGTH: 50
<212> TYPE: DNA
<213> ORGANISM: Artificial sequence
<220> FEATURE:
<223> OTHER INFORMATION: oligonucleotide

<400> SEQUENCE: 28
tacgactcag gctttgccgg gtatgactca ggctttgccg ggtaacaggg           50

<210> SEQ ID NO 29
<211> LENGTH: 34
<212> TYPE: DNA
<213> ORGANISM: Artificial sequence
<220> FEATURE:
<223> OTHER INFORMATION: oligonucleotide

<400> SEQUENCE: 29
gggtagggcg ggaagttact gtcttactgt cgta                           34

<210> SEQ ID NO 30
<211> LENGTH: 23
<212> TYPE: DNA
<213> ORGANISM: Artificial sequence
<220> FEATURE:
<223> OTHER INFORMATION: oligonucleotide

<400> SEQUENCE: 30
tacgactcag gctttgccgg gta                                       23

<210> SEQ ID NO 31
<211> LENGTH: 10
<212> TYPE: DNA
<213> ORGANISM: Artificial sequence
<220> FEATURE:
<223> OTHER INFORMATION: oligonucleotide

<400> SEQUENCE: 31

```
tactgtcgta                                                          10
```

<210> SEQ ID NO 32
<211> LENGTH: 22
<212> TYPE: DNA
<213> ORGANISM: Artificial sequence
<220> FEATURE:
<223> OTHER INFORMATION: oligonucleotide

<400> SEQUENCE: 32

```
gactcaggct ttgccgggta ac                                            22
```

<210> SEQ ID NO 33
<211> LENGTH: 9
<212> TYPE: DNA
<213> ORGANISM: Artificial sequence
<220> FEATURE:
<223> OTHER INFORMATION: oligonucleotide

<400> SEQUENCE: 33

```
gttactgtc                                                            9
```

<210> SEQ ID NO 34
<211> LENGTH: 39
<212> TYPE: DNA
<213> ORGANISM: Artificial sequence
<220> FEATURE:
<223> OTHER INFORMATION: oligonucleotide

<400> SEQUENCE: 34

```
ctccttcaac gaagtgggtc tccttcaacg aagtgggtc                          39
```

<210> SEQ ID NO 35
<211> LENGTH: 17
<212> TYPE: DNA
<213> ORGANISM: Artificial sequence
<220> FEATURE:
<223> OTHER INFORMATION: oligonucleotide

<400> SEQUENCE: 35

```
gacaaggtga caaggag                                                  17
```

<210> SEQ ID NO 36
<211> LENGTH: 8
<212> TYPE: DNA
<213> ORGANISM: Artificial sequence
<220> FEATURE:
<223> OTHER INFORMATION: oligonucleotide
<220> FEATURE:
<221> NAME/KEY: misc_feature
<222> LOCATION: (2)..(2)
<223> OTHER INFORMATION: n = a, c, t, aa, ac, at, cc, ca, ct, ta, tc, or
      tt, or the nucleotide may be absent
<220> FEATURE:
<221> NAME/KEY: misc_feature
<222> LOCATION: (5)..(5)
<223> OTHER INFORMATION: n = a, c, t, aa, ac, at, cc, ca, ct, ta, tc, or
      tt, or the nucleotide may be absent

<400> SEQUENCE: 36

```
gnggnggg                                                             8
```

<210> SEQ ID NO 37
<211> LENGTH: 7
<212> TYPE: DNA
<213> ORGANISM: Artificial sequence
<220> FEATURE:
<223> OTHER INFORMATION: oligonucleotide

```
<220> FEATURE:
<221> NAME/KEY: misc_feature
<222> LOCATION: (4)..(4)
<223> OTHER INFORMATION: n = a, c, t, aa, ac, at, cc, ca, ct, ta, tc, or
      tt, or the nucleotide may be absent

<400> SEQUENCE: 37 gggnggg                                                                    7

<210> SEQ ID NO 38
<211> LENGTH: 9
<212> TYPE: DNA
<213> ORGANISM: Artificial sequence
<220> FEATURE:
<223> OTHER INFORMATION: oligonucleotide

<400> SEQUENCE: 38 gtggagggt                                                                  9

<210> SEQ ID NO 39
<211> LENGTH: 8
<212> TYPE: DNA
<213> ORGANISM: Artificial sequence
<220> FEATURE:
<223> OTHER INFORMATION: oligonucleotide

<400> SEQUENCE: 39 gggagggt                                                                   8

<210> SEQ ID NO 40
<211> LENGTH: 8
<212> TYPE: DNA
<213> ORGANISM: Artificial sequence
<220> FEATURE:
<223> OTHER INFORMATION: oligonucleotide

<400> SEQUENCE: 40 gggcgggt                                                                   8

<210> SEQ ID NO 41
<211> LENGTH: 9
<212> TYPE: DNA
<213> ORGANISM: Artificial sequence
<220> FEATURE:
<223> OTHER INFORMATION: oligonucleotide

<400> SEQUENCE: 41 agggacggg                                                                  9

<210> SEQ ID NO 42
<211> LENGTH: 8
<212> TYPE: DNA
<213> ORGANISM: Artificial sequence
<220> FEATURE:
<223> OTHER INFORMATION: oligonucleotide

<400> SEQUENCE: 42 agggcggg                                                                   8

<210> SEQ ID NO 43
<211> LENGTH: 16
<212> TYPE: DNA
<213> ORGANISM: Artificial sequence
<220> FEATURE:
<223> OTHER INFORMATION: oligonucleotide

<400> SEQUENCE: 43
```

```
gggcgggtag ggcggg                                                       16

<210> SEQ ID NO 44
<211> LENGTH: 3
<212> TYPE: DNA
<213> ORGANISM: Artificial sequence
<220> FEATURE:
<223> OTHER INFORMATION: oligonucleotide

<400> SEQUENCE: 44 ggg                                                                      3

<210> SEQ ID NO 45
<211> LENGTH: 12
<212> TYPE: DNA
<213> ORGANISM: Artificial sequence
<220> FEATURE:
<223> OTHER INFORMATION: oligonucleotide

<400> SEQUENCE: 45
gggtagggcg gg                                                           12
```

MATERIAL AND METHOD FOR COLORIMETRIC DETECTION OF SMALL-MOLECULE TARGETS

CROSS-REFERENCE TO A RELATED APPLICATION

This application is a continuation application of U.S. patent application Ser. No. 16/179,336, filed Nov. 2, 2018, which is incorporated herein by reference in its entirety.

GOVERNMENT SUPPORT

This invention was made with government support under DA036821 awarded by the National Institutes of Health. The government has certain rights in the invention.

SEQUENCE LISTING

The Sequence Listing for this application is labeled "SeqList-06Jan21_ST25.txt," which was created on Jan. 6, 2021, and is 10 KB. The Sequence Listing is incorporated herein by reference in its entirety.

BACKGROUND OF THE INVENTION

Small molecules are important targets with the potential of clinical or commercial applications such as medical diagnostics, environmental monitoring, and forensic science. Thus, efforts to develop methods for portable, low-cost, and quantitative on-site detection of a broad range of small molecules are gaining momentum.

Cocaine is a central nervous system stimulant that increases levels of dopamine and potently inhibits neurotransmitter reuptake at the synapse. Abuse of cocaine has been shown to cause anxiety, paranoia, mood disturbances, organ damage, and violent behavior.

Synthetic cathinones (also known as bath salts) are designer drugs sharing a similar core structure with amphetamines and 3, 4-methylenedioxy-methamphetamine (MDMA). They are highly addictive central nervous system stimulants, and are associated with many negative health consequences, including even death. Although these drugs have emerged only recently, abuse of bath salts has become a threat to public health and safety due to their severe toxicity, increasingly broad availability, and difficulty of regulation. More importantly, there is currently no reliable presumptive test for any synthetic cathinone. Chemical spot tests used to detect conventional drugs such as cocaine, methamphetamine, and opioids show no cross-reactivity to synthetic cathinones.

Methods that are highly sensitive and selective, including high-performance liquid chromatography (HPLC) and gas chromatography-mass spectrometry (GC-MS), have been used for the detection of small molecules. However, these methods are time-consuming and require expensive reagents, advanced equipment, complex sample preparation, and/or trained operators.

Various immunoassays have also been developed for the detection of small molecules such as cocaine and/or its major metabolite benzoylecgonine in biofluids, including the enzyme-linked immunosorbent assay (ELISA). Unfortunately, the use of immunoassays for the detection of designer drugs is often limited because of the high cost of generating new antibodies and issues with narrow target binding-spectrum and poor specificity.

Nucleic acid-based bioaffinity elements, known as aptamers, can be isolated in vitro through systematic evolution of ligands by exponential enrichment (SELEX) processes to bind various targets with high specificity and affinity, including proteins, metal ions, small molecules, and even whole cells. They have gained considerable attention as bio-recognition elements with diverse applications in areas such as drug screening, medical diagnostics, and environmental monitoring. This is in part because aptamers are chemically stable, offering long shelf lives, and can be synthesized at a low cost with high reproducibility. Also, aptamers can be engineered to have tunable target-binding affinities or various functionalities. These advantages make aptamers ideal for use in biosensors.

Among the numerous aptamer-based sensing platforms, colorimetric assays are especially desirable for on-site detection, as they can be interpreted by the naked eye and do not require any specialized equipment to obtain a readout. For example, gold nanoparticles (AuNPs) have been widely employed with aptamers as sensitive colorimetric signal reporters for naked-eye small-molecule detection. G-quadruplex-structured DNA enzymes (DNAzymes) are alternative signal reporters for colorimetric aptamer-based assays. However, most of these assays offer only limited capabilities for naked-eye detection, because the resulting absorbance changes can only be detected by instruments.

Therefore, there is a need for methods and materials for rapid, naked-eye small-molecule detection. Assays using such materials and methods provide essential features such as ease of use, cost-effectiveness, rapid turnaround time and superior sensitivity and specificity.

BRIEF SUMMARY OF THE INVENTION

The subject invention provides methods, assays, and products for rapid, naked-eye detection of small molecules in a sample, in particular, in both clinical and field settings. The subject invention is based on an aptamer sensor that reports the presence of small-molecule target such as cocaine and synthetic cathinones via a sensitive colorimetric signal for naked-eye detection. Specifically, exemplified herein is a method for detecting cocaine and synthetic cathinones.

In one embodiment, the aptamer sensor is a CBSAzyme-based sensor having both target-mediated cooperative behavior of the CBSA and peroxidase-mimicking catalytic activity of DNAzyme.

The CBSAzyme-based sensor comprises a long fragment and a short fragment, the long fragment comprising a first segment of a split DNAzyme and a long fragment of a CBSA, the short fragment comprising a second segment of the split DNAzyme and a short fragment of the CBSA. The two fragments of the CBSAzyme remain separate in the absence of the small-molecule target, but effectively assemble in the presence of the small-molecule target. The assembly of the two fragments of the CBSAzyme activates the DNAzyme that subsequently catalyzes the oxidation of 2,2'-azinobis(3-ethylbenzthiazo-line)-6-sulfonic acid (ABTS), producing a visible color change from colorless to dark green that reveals the presence of the target within minutes.

The subject invention also provides methods of using the CBSAzyme-based assays for rapid and naked-eye detection of small-molecule targets in a sample. The method comprises contacting the sample with a CBSAzyme-based sensor selective for the small-molecule target and detecting the small-molecule target in the sample by measuring a signal generated from a signal reporter. In a specific embodiment, the signal reporter is ABTS, and the signal generated from the signal reporter is a color change resulting from the $H_2O_2$-mediated oxidation of ABTS to ABTS$^{\bullet+}$ by the peroxidase-mimicking catalytic activity of the assembled split DNAzyme. Thus, a change in color is indicative of the presence and quantity of the small-molecule target in the sample.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 6A-6C show the effect of DNAzyme split mode on enzyme catalytic activity. (6A) Constructing the 1:3 mode split DNAzyme and subsequent conjugation to COC-5334 via dinucleotide linkers to generate CBSAzyme-5334-13 (LF: SEQ ID NO: 18; SF: SEQ ID NO: 19). Structures and time-course absorbance measurements for (6B) CBSAzyme-5334-13 and (6C) CBSAzyme-5334-22 in the absence and presence of 250 μM cocaine. [Each fragment]=1 μM.

FIGS. 7A-7B show the determination of the enzyme kinetics of CBSAzyme-5334-22 and CBSAzyme-5334-13. (7A) The initial reaction rate of the CBSAzymes was plotted against the concentration of ABTS. (7B) The Michaelis-Menten constant ($K_M$) and turnover number ($k_{cat}$) in the presence and absence of cocaine were obtained from the plotted curves.

FIGS. 16A-16B show the comparison of the target-responsiveness of COC-CBSAzyme (LF: SEQ ID NO: 20; SF: SEQ ID NO: 19) and SAzyme-334 (LF: SEQ ID NO: 22; SF: SEQ ID NO: 23). (16A) Structures of COC-CBSAzyme and SAzyme-334. (16B) Photographs of samples containing COC-CBSAzyme and SAzyme-334 in the presence of various concentrations of cocaine (0-1,000 µM) after 2 minutes (top panel) and 15 minutes (bottom panel) of reaction.

FIGS. 17A-17C show the specificity of the CBSAzyme-based assay for cocaine detection. (17A) Chemical structures of interferents tested in the assay. (17B) Absorbance of samples at 418 nm after 15 minutes of reaction containing various interferents (250 µM). (17C) Photographs of samples containing various interferents (250 µM) after 15 minutes of reaction.

FIGS. 18A-18C show the engineering and characterization of an MDPV-binding CBSA. (18A) An isolated MDPV-binding aptamer (SEQ ID NO: 24) (I) was used to generate a pair of split aptamers with destabilized stems (II), which were then merged to create MDPV-6335 (LF: SEQ ID NO: 25; SF: SEQ ID NO: 26) (III). (18B) Scheme of a MDPV fluorescence assay using a fluorophore-quencher modified version of MDPV-6335 (LF: SEQ ID NO: 25; SF: SEQ ID NO: 27). (18C) Binding curve of MDPV-6335 generated using 0-3,000 µM MDPV and the calculated values for $K_{1/2}$ and $n_H$ using the Hill Equation.

FIGS. 19A-19B show the design and performance of an MDPV-binding CBSAzyme (LF: SEQ ID NO: 28; SF: SEQ ID NO: 29). (19A) Engineering of MDPV-CBSAzyme using MDPV-6335 and the optimized split DNAzyme fragments (SEQ ID NO: 44 and SEQ ID NO: 45). In the presence of MDPV, the two CBSAzyme fragments assemble, such that the DNAzyme can catalyze the oxidation of ABTS to generate the green-colored ABTS$^{\bullet+}$. (19B) Time-course absorbance measurement at 418 nm with reaction buffer containing 1 µM MDPV-CBSAzyme in the presence and absence of 250 µM MDPV.

FIGS. 21A-21C show utilizing MDPV-CBSAzyme for the visual detection of MDPV. (21A) Time-dependent absorbance change at 418 nm with (1) reaction buffer alone, (2) hemin alone, (3) the short fragment plus hemin, (4) the long fragment with hemin, and both fragments with hemin in the (5) absence or (6) presence of MDPV. (21B) Photographs of samples containing different concentrations of MDPV (0 to 1,000 µM) after 15 minutes of reaction. (21C) Assay calibration curve with MDPV concentrations ranging from 0 to 1,000 µM. Inset represents linear range from 0 to 10 µM. [Each fragment]=1 µM

BRIEF DESCRIPTION OF SEQUENCES

Figure 1A:
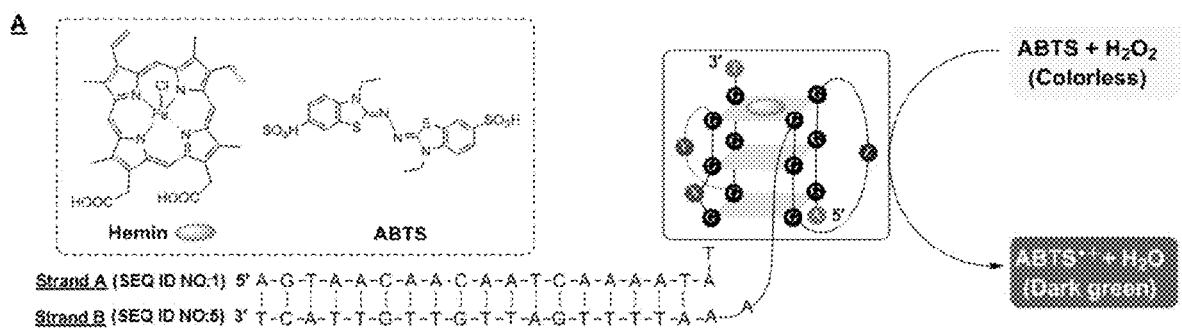
FIGS. 1A-1C show optimizing the activity of a split G-quadruplex-structured DNAzyme using a duplex DNA template. (1A) Structures of hemin, ABTS, and the duplex DNA-DNAzyme conjugate formed by strands A (SEQ ID NO: 1) and B (SEQ ID NO: 5) (left) and the scheme for DNAzyme-mediated oxidation of ABTS to produce the green-colored ABTS$^{\bullet+}$ (right). X, Y and Z indicate selected modification sites within the spacers between GGG repeats. (1B, 1C) (left) Structures of the assembled split DNAzyme modules of (1B) A0 (SEQ ID NO: 38) -B0 (SEQ ID NO: 41), A1 (SEQ ID NO: 39) -B0 (SEQ ID NO: 41), A2 (SEQ ID NO: 40) -B0 (SEQ ID NO: 41), (1C) A2 (SEQ ID NO: 40) -B0 (SEQ ID NO: 41), and A2 (SEQ ID NO: 40)-B1 (SEQ ID NO: 42) and (right) reaction rates of each DNAzyme in terms of nanomolar ABTS$^{\bullet+}$ produced per second.

SEQ ID NOs: 1-7 are sequences of duplex DNA-DNAzyme conjugates contemplated for use according to the subject invention.

SEQ ID NO: 8 is the DNA sequence of the long fragment of aptamer COC-5335 contemplated for use according to the subject invention.

SEQ ID NO: 9 is the DNA sequence of the short fragment of aptamer COC-5335 contemplated for use according to the subject invention.

SEQ ID NO: 10 is the DNA sequence of the long fragment of COC-CBSAzyme-5335-22 contemplated for use according to the subject invention.

SEQ ID NO: 11 is the DNA sequence of the short fragment of COC-CBSAzyme-5335-22 contemplated for use according to the subject invention.

SEQ ID NO: 12 is the DNA sequence of the long fragment of COC-CBSAzyme-5334-22 contemplated for use according to the subject invention.

SEQ ID NO: 13 is the DNA sequence of the short fragment of COC-CBSAzyme-5334-22 contemplated for use according to the subject invention.

SEQ ID NO: 14 is the DNA sequence of the long fragment of COC-CBSAzyme-5333-22 contemplated for use according to the subject invention.

SEQ ID NO: 15 is the DNA sequence of the short fragment of COC-CBSAzyme-5333-22 contemplated for use according to the subject invention.

SEQ ID NO: 16 is the DNA sequence of the short fragment of aptamer COC-5334 contemplated for use according to the subject invention.

SEQ ID NO: 17 is the DNA sequence of the long fragment of aptamer COC-5334 contemplated for use according to the subject invention.

SEQ ID NO: 18 is the DNA sequence of a long fragment of COC-CBSAzyme-5334-13 with a AT linker contemplated for use according to the subject invention.

SEQ ID NO: 19 is the DNA sequence of a short fragment of COC-CBSAzyme-5334-13 with a AA linker contemplated for use according to the subject invention.

SEQ ID NO: 20 is the DNA sequence of a long fragment of COC-CBSAzyme-5334-13 with a A linker contemplated for use according to the subject invention.

SEQ ID NO: 21 is the DNA sequence of a short fragment of COC-CBSAzyme-5334-13 with a A linker contemplated for use according to the subject invention.

SEQ ID NO: 22 is the DNA sequence of the long fragment of SAzyme-334 contemplated for use according to the subject invention.

SEQ ID NO: 23 is the DNA sequence of the short fragment of SAzyme-334 contemplated for use according to the subject invention.

SEQ ID NO: 24 is the DNA sequence of a MDPV-binding aptamer contemplated for use according to the subject invention.

SEQ ID NO: 25 is the DNA sequence of the long fragment of MDPV-6335 contemplated for use according to the subject invention.

SEQ ID NO: 26 is the DNA sequence of a short fragment of MDPV-6335 contemplated for use according to the subject invention.

SEQ ID NO: 27 is the DNA sequence of a short fragment of MDPV-6335 with fluorophore-quencher modifications contemplated for use according to the subject invention.

SEQ ID NO: 28 is the DNA sequence of a long fragment of MDPV-CBSAzyme contemplated for use according to the subject invention.

SEQ ID NO: 29 is the DNA sequence of a short fragment of MDPV-CBSAzyme contemplated for use according to the subject invention.

SEQ ID NO: 30 is the DNA sequence of a long fragment of a parent split MDPV aptamer contemplated for use according to the subject invention.

SEQ ID NO: 31 is the DNA sequence of a short fragment of a parent split MDPV aptamer contemplated for use according to the subject invention.

SEQ ID NO: 32 is the DNA sequence of a long fragment of a parent split MDPV aptamer contemplated for use according to the subject invention.

SEQ ID NO: 33 is the DNA sequence of a short fragment of a parent split MDPV aptamer contemplated for use according to the subject invention.

SEQ ID NO: 34 is the DNA sequence of the long fragment of COC-5333 contemplated for use according to the subject invention.

SEQ ID NO: 35 is the DNA sequence of the short fragment of COC-5333 contemplated for use according to the subject invention.

SEQ ID NOs: 36-42 are the sequences of fragments of the split DNAzyme contemplated for use according to the subject invention.

SEQ ID NO: 43 is the sequence of a DNAzyme contemplated for use according to the subject invention.

SEQ ID NOs: 44-45 are DNA sequences of segments of a split DNAzyme contemplated for use according to the subject invention.

DETAILED DESCRIPTION OF THE INVENTION

The subject invention provides methods, assays, and products for rapid, naked-eye detection of small molecules in a sample, in particular, in both clinical and field settings. In one embodiment, the sample is a biological sample of a subject. In specific embodiments, the biological sample is selected from blood, plasma, urine, tears, sweat and saliva. The subject may be any animal or human, preferably, a human. The subject may also be any animal including, but not limited to, non-human primates, rodents, dogs, cats, horses, cattle, pigs, sheep, goats, chickens, guinea pigs, hamsters and the like.

In one embodiment, the sample is an environmental sample, for example, water, soil, air, or plant sample. In another embodiment, the sample is a seized drug sample, for instance, a street drug sample seized by law enforcement or government officials.

Small Molecules

The term "target," "small molecule," or "small-molecule target," as used herein, includes any molecule capable of being detected using an aptamer technique. In certain embodiments, the small molecule has a molecular weight less than 1000 Daltons, less than 900 Daltons, less than 800 Daltons, less than 700 Daltons, less than 600 Daltons, less than 500 Daltons, less than 400 Daltons, less than 300 Daltons, or less than 200 Daltons.

In specific embodiments, the small-molecule target may be an amino acid, an amino acid-related molecule, a peptide, a steroid, a lipid, a sugar, a carbohydrate, a biomarker, a drug molecule, a drug metabolite, a coenzyme, a nucleotide (nt), a nucleotide-related molecule, a pyridine nucleotide, a cyclic nucleotide, or a cyclic dinucleotide. In other embodiments, the small-molecule target may be an infective agent, antigen, toxin, disease biomarker, or a specific metal ion.

In one embodiment, the small molecule is a drug molecule. In specific embodiments, the drug molecule is cocaine or a cocaine derivative/metabolite. The cocaine derivative may or may not have the core structure of cocaine. Exemplary cocaine derivatives/metabolites include, but are not limited to, 4-fluorococaine, 2-hydroxycocaine, 3-(p-fluorobenzoyloxy)tropane (pFBT), cocaethylene, norcocaine, procaine, and dimethocaine.

In one embodiment, the drug molecule is a cathinone, a cathinone derivative, or synthetic cathinone, such as a ring-substituted cathinone derivative or synthetic cathinone. The synthetic cathinone has a general structure of formula (I)

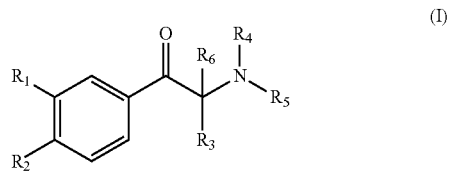

wherein $R_1$ and $R_2$, are each independently selected from the group consisting of hydrogen, alkyl, aryl, heteroaryl, cycloalkyl, cycloalkenyl, heterocycloalkyl, alkenyl, alkynyl, haloalkyl, acyl, alkoxy, halogen, and hydroxylalkyl; $R_3$ is hydrogen or alkyl. $R_4$, and $R_5$ are each independently selected from the group consisting of hydrogen, alkyl, aryl, heteroaryl, cycloalkyl, cycloalkenyl, heterocycloalkyl, alkenyl, alkynyl, haloalkyl, acyl, halogen, and hydroxylalkyl; and $R_6$ is hydrogen or alkyl.

In a further embodiment, $R_1$ and $R_2$ are independently a halogen such as fluorine, chlorine, bromine or iodine.

In some embodiments, $R_1$ and $R_2$, taken together with the carbon atoms to which they are attached, form a substituted or unsubstituted 5- or 6-membered homocyclic or heterocyclic ring. For example, $R_1$ and $R_2$ may form a methylenedioxy group or aromatic group such as a benzene ring.

In other embodiments, $R_4$ and $R_5$, taken together with the nitrogen atom to which they are attached, form a substituted or unsubstituted 5- or 6-membered heterocyclic ring. For example, $R_4$ and $R_5$ may form a pyrrolidino group.

As used herein, "alkyl" means linear saturated monovalent radicals of at least one carbon atom or a branched saturated monovalent of at least three carbon atoms. It may include hydrocarbon radicals of at least one carbon atom, which may be linear. Examples include, but are not limited to, methyl, ethyl, propyl, 2-propyl, n-butyl, iso-butyl, tert-butyl, pentyl, hexyl, and the like.

As used herein, "acyl" means a radical —C(O)R where R includes, but is not limited to, hydrogen, alkyl or cycloalkyl, and heterocycloalkyl. Examples include, but are not limited to, formyl, acetyl, ethylcarbonyl, and the like. An aryl group may be substituted or unsubstituted.

As used herein, "alkylamino" means a radical —NHR or —NR2 where each R is, independently, an alkyl group. Examples include, but are not limited to, methylamino, (1-methylethyl)amino, dimethyl amino, methylethylamino, di(1-methylethyl)amino, and the like. An alkylamino may be substituted or unsubstituted.

As used herein, "hydroxyalkyl" means an alkyl radical substituted with one or more hydroxy groups. Representative examples include, but are not limited to, hydroxymethyl, 2-hydroxyethyl; 2-hydroxypropyl; 3-hydroxypropyl; 1-(hydroxymethyl)-2-methylpropyl; 2-hydroxybutyl; 3-hydroxybutyl; 4-hydroxybutyl; 2,3-dihydroxypropyl; 2-hydroxy-1-hydroxymethylethyl; 2,3-dihydroxybutyl; 3,4-dihydroxybutyl and 2-(hydroxymethyl)-3-hydroxy-propyl; preferably 2-hydroxyethyl; 2,3-dihydroxypropyl and 1-(hydroxymethyl) 2-hydroxyethyl. A hydroxyalkyl may be substituted or unsubstituted.

As used herein, "alkenyl" refers to a straight or branched hydrocarbon chain containing one or more double bonds. The alkenyl group may have 2 to 9 carbon atoms, although the present definition also covers the occurrence of the term "alkenyl" where no numerical range is designated. The alkenyl group may also be a medium size alkenyl having 2 to 9 carbon atoms. The alkenyl group could also be a lower alkenyl having 2 to 4 carbon atoms. The alkenyl group may be designated as "$C_{2-4}$ alkenyl" or similar designations. By way of example only, "$C_{2-4}$ alkenyl" indicates that there are two to four carbon atoms in the alkenyl chain, i.e., the alkenyl chain is selected from ethenyl; propen-1-yl; propen-2-yl; propen-3-yl; buten-1-yl; buten-2-yl; buten-3-yl; buten-4-yl; 1-methyl-propen-1-yl; 2-methyl-propen-1-yl; 1-ethyl-ethen-1-yl; 2-methyl-propen-3-yl; buta-1,3-dienyl; buta-1,2,-dienyl and buta-1,2-dien-4-yl. Typical alkenyl groups include, but are in no way limited to, ethenyl, propenyl, butenyl, pentenyl, and hexenyl, and the like.

As used herein, "alkynyl" refers to a straight or branched hydrocarbon chain comprising one or more triple bonds. The alkynyl group may have 2 to 9 carbon atoms, although the present definition also covers the occurrence of the term "alkynyl" where no numerical range is designated. The alkynyl group may also be a medium size alkynyl having 2 to 9 carbon atoms. The alkynyl group could also be a lower alkynyl having 2 to 4 carbon atoms. The alkynyl group may be designated as "$C_{2-4}$ alkynyl" or similar designations. By way of example only, "$C_{2-4}$ alkynyl" indicates that there are two to four carbon atoms in the alkynyl chain, e.g., the alkynyl chain is selected from ethynyl, propyn-1-yl, propyn-2-yl, butyn-1-yl, butyn-3-yl, butyn-4-yl, and 2-butynyl. Typical alkynyl groups include, but are in no way limited to, ethynyl, propynyl, butynyl, pentynyl, and hexynyl, and the like.

As used herein, "cycloalkyl" means a fully saturated carbocyclyl ring or ring system. Examples include, but are not limited to, cyclopropyl, cyclobutyl, cyclopentyl, and cyclohexyl.

As used herein, "aryl" refers to a carbocyclic (all carbon) monocyclic or multicyclic aromatic ring system (including fused ring systems where two carbocyclic rings share a chemical bond). The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, phenyl, benzyl, α-naphthyl, β-naphthyl, biphenyl, anthryl, tetrahydronaphthyl, fluorenyl, indanyl, biphenylenyl, and acenaphthenyl. Preferred aryl groups are phenyl and naphthyl.

As used herein, "heteroaryl" refers to an aromatic ring or ring system (i.e., two or more fused rings that share two adjacent atoms) that comprise(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members (i.e., the number of atoms making up the ring backbone, including carbon atoms and heteroatoms), although the present definition also covers the occurrence of the term "heteroaryl" where no numerical range is designated. Examples of heteroaryl rings include, but are not limited to, furyl, thienyl, phthalazinyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, triazinyl, quinolinyl, isoquinlinyl, benzimidazolyl, benzoxazolyl, benzothiazolyl, indolyl, isoindolyl, and benzothienyl.

As used herein, "haloalkyl" refers to an alkyl group, in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl and 1-chloro-2-fluoromethyl, 2-fluoroisobutyl. A haloalkyl may be substituted or unsubstituted.

As used herein, a "substituted" group may be substituted with one or more group(s) individually and independently selected from alkyl, alkenyl, alkynyl, cycloalkyl, cycloalkenyl, cycloalkynyl, benzyl, substituted benzyl, aryl, heteroaryl, heteroalicyclyl, aralkyl, heteroaralkyl, (heteroalicyclyl)alkyl, hydroxy, protected hydroxyl, alkoxy, aryloxy, acyl, mercapto, alkylthio, arylthio, cyano, halogen, thiol, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, an amino, a mono-substituted amino group and a di-substituted amino group, and protected derivatives thereof.

As used herein, "halogen" refers to an atom of fluorine, chlorine, bromine or iodine.

As used herein, "homocyclic ring" refers to cycloalkyl or aryl.

As used herein, "heterocyclic ring" refers to a ring, which may contain 1 to 4 heteroatoms selected from among nitrogen, oxygen, sulfur and other atoms in addition to carbon atoms.

Exemplary cathinones or synthetic cathinones include, but are not limited to, 3, 4-methylenedioxypyrovalerone (MDPV); 4'-methyl-α-pyrrolidinohexanophenone (MPHP); naphyrone; methylone; ethylone; butylone; pentylone; mephedrone; mexedrone; buphedrone; pentedrone; hexedrone; heptedrone; α-pyrrolidinopropiophenone (α-PPP); 4'-methyl-α-pyrrolidinopropiophenone (M-α-PPP); 3',4'-methylenedioxy-α-pyrrolidinopropiophenone (MDPPP); 1-phenyl-2-(1-pyrrolidinyl)-1-pentanone (α-PVP); α-pyrrolidinohexiophenone (α-PHP); α-pyrrolidinoheptiophenone (α-PHpP, PV8); diethylpropion; pyrovalerone; dimethylcathinone; diethylcathinone; methcathinone; ethcathinone; 3-methylmetheathinone (3-MMC); 4-methylethcathinone (4-MEC); 3-chloromethcathinone (3-CMC); 4-chloromethe-athinone (4-CMC); n-ethyl-nor-pentedrone (NEP); 3,4-methylenedioxy-α-pyrrolidinobutiophenone (MDPBP); 4-methyl-α-pyrrolidinobutiophenone (MEPBP); 4-fluorometheathinone (4-FMC); n-ethyl-nor-hexedrone (Hexen); n-ethyl-nor-heptedrone; 4-ethylpentedrone; 4-methyl-NEP; and n-ethyl-nor-pentylone.

In a specific embodiment, the synthetic cathinone is selected from MDPV, penthylone, mephedrone, naphyrone, MDPBP, methylone, methedrone, ethylone, butylone, MPHP, and MEPBP.

Aptamer-Based Sensors

The subject invention provides aptamer-based sensors for rapid and naked-eye detection of small-molecule targets. In one embodiment, the aptamer-based sensor is a CBSAzyme-based sensor having both target-mediated cooperative behavior of the cooperative binding split aptamers (CBSAs) and peroxidase-mimicking catalytic activity of DNAzyme.

In one embodiment, the CBSAzyme-based sensor comprises a CBSA-DNAzyme conjugate (CBSAzyme), which comprises or consists of a pair of highly target-responsive CBSAs grafted to an engineered split DNAzyme with peroxidase-mimicking catalytic activity. The CBSAzyme-based sensor can further comprise a signal reporter, which comprises a mixture of a peroxidase substrate and $H_2O_2$.

In one embodiment, the CBSAzyme comprises a split DNAzyme grafted to a pair of CBSA fragments. In a further embodiment, the CBSAzyme comprises a first fragment and a second fragment, the first fragment comprising a first segment of a split DNAzyme and a long fragment of a CBSA; and the second fragment comprising a second segment of the split DNAzyme and a short fragment of the CBSA.

The two fragments of the CBSAzyme remain separate in the absence of a small-molecule target, but effectively assemble in the presence of the small-molecule target. The assembly of the two fragments of the CBSAzyme activates the split DNAzyme that subsequently catalyzes the oxidation of a peroxidase substrate in the presence of $H_2O_2$, producing a signal change (e.g., a visible color change from colorless to dark green) that reveals the presence and quantity of the target within minutes.

In one embodiment, the peroxidase substrate is selected from 3,3',5,5'-tetramethylbenzidine (TMB), ABTS, N-(4-Aminobutyl)-N-ethylisoluminol, 3-amino-9-ethylcarbazole, 3-amino-9-ethylcarbazole, 4-aminophthalhydrazide, 5-aminosalicylic acid, 2,2'-azino-bis(3-ethylbenzothiazoline-6-sulfonic acid), 4-chloro-1-naphthol, 4-chloro-7-nitrobenzofurazan, 3,3'-diaminobenzidinetetrahydrochloride, o-dianisidinedihydrochloride, iodonitrotetrazolium chloride, luminol, 1-(4,5-dimethylthiazol-2-yl)-3,5-diphenylformazan, nitrotetrazolium blue chloride, o-phenylenediamine, trans-5-phenyl-4-pentenyl hydroperoxide, pyrogallol, tetranitroblue tetrazolium chloride, and tetrazolium Violet. In a preferred embodiment, the peroxidase substrate is ABTS.

In one embodiment, the CBSAzyme further comprises linkers between the fragments of the CBSA and the segments of DNAzyme, which include a first linker between the long fragment of the CBSA and the first segment of the split DNAzyme, and a second linker between the short fragment of the CBSA and the second segment of the split DNAzyme.

The linkers are nucleotide sequences comprising at least one, at least two, at least three, at least four, at least five, at least six, at least seven or at least eight nucleotides. In a preferred embodiment, the linkers comprise one or two nucleotides. The first and second linkers may have same or different sequences. In a specific embodiment, the linkers are selected from A, C, T, AA, AC, AT, CC, CA, CT, TA, TC, and TT.

In one embodiment, the CBSAzyme-based sensor further comprises a compound or cofactor that contributes to the activity of the split DNAzyme. In a specific embodiment, the compound is hemin.

Aptamers

Aptamers are nucleic acid molecules characterized by the ability to bind to a target molecule with high specificity and high affinity. Almost every aptamer identified to date is a non-naturally occurring molecule. Aptamers to a given target may be identified and/or produced by the method of systematic evolution of ligands by exponential enrichment (SELEX). In one embodiment, the aptamer according to the subject invention is isolated by SELEX for the small molecule of interest.

In one embodiment, the aptamer is an oligonucleotide, such as DNA or RNA molecules and may be single-stranded or double-stranded. In a preferred embodiment, the aptamer is a DNA aptamer.

The aptamer may be partially or fully folded to form various secondary structures (e.g., stems, loops, bulges, pseudoknots, G-quadruplexes and kissing hairpins), which in turn can form unique three-dimensional architectures able to specifically recognize their targets by exploiting a variety of interactions-such as hydrophobic and electrostatic interactions, hydrogen bonding, van der Waals forces, and 7-7 stacking as well as shape complementarity.

As used herein, the terms "polynucleotide," "nucleotide," "oligonucleotide," and "nucleic acid" refer to a nucleic acid comprising DNA, RNA, derivatives thereof, or combinations thereof.

In certain embodiments, the aptamer according to the present invention may comprise at least 10, at least 20, at least 30, at least 40, at least 50, at least 60, at least 70, or at least 80 nucleotides. The aptamer according to the present invention, preferably, comprises 10 to 200 nucleotides, preferably 15 to 150 nucleotides, more preferably 20 to 100 nucleotides, most preferably, 30 to 60 nucleotides.

In certain embodiments, the aptamer according to the present invention has a minimum length of, for example, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides. The aptamer according to the present invention may have a maximum length of, for example, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, or 150 nucleotides. The aptamer according to the present invention may have a length of, for example, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides.

In some embodiments, the aptamers according to the subject invention have free ends. For example, the 3' and 5' ends may not be ligated to form a loop, although they may be conjugated to other molecules or otherwise modified. The aptamers may adopt a tertiary structure such as a hairpin loop.

In certain embodiments, the aptamer according to the subject invention comprises at least one stems, two stems, or three stems. Preferably, the aptamer comprises three stems. Each stem may be fully or partially complementary. Each stem may comprise the same or a different number of nucleotides. Exemplary lengths of each stem may be 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides.

In one embodiment, each stem comprises the same or a different number of base pairs (bps). Each stem may have a minimum of, for example, 1, 2, 3, 4, 5, 6, 7, 8, 9, 10, 11, or 12 base pairs. Each stem may have a maximum of, for example, 13, 14, 15, 16, 17, 18, 19, 20, 21, 22, 23, 24, 25, 26, 27, 28, 29, or 30 base pairs. Each stem according to the present invention may have a number of, for example, 1, 2, 3, 4, 5, 6, 7, 8, 9, 10, 11, 12, 13, 14, or 15 base pairs. A partially complementary stem may comprise more than one wobble base pair, including, but not limited to, G-U, and T-G.

Each of the stems may independently connect to a loop at the end, forming a stem-loop structure. The aptamer may thereby comprise at least one, two, or three stem-loop structures. The stem-loop structure according to the present invention may have a minimum length of, for example, 5, 6, 7, 8, 9, 10, 11, 12, 13, 14, 15, 16, 17, 18, 19, 20, 21, 22, 23, 24, or 25 nucleotides. The stem-loop structure may have a maximum length of, for example, 40, 41, 42, 43, 44, 45, 46, 47, 48, 49, 50, 51, 52, 53, 54, 55, 56, 57, 58, 59, 60, 61, 62, 63, 64, or 65 nucleotides.

In one embodiment, the aptamer comprises at least one junction, which is formed when two or more stems meet. In certain embodiments, the junction may be a loop between two stems, or a three-way junction (TWJ). The junction in an aptamer can serve as a binding domain for a small-molecule target.

The junction may have a minimum length of, for example, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides. The junction may have a maximum length of, for example, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleotides. The junction may comprise, for example, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides.

In a specific embodiment, the aptamer comprises a TWJ-binding domain. In some embodiments, the aptamer is a monomer, dimer, trimer, or tetramer. Such aptamer can comprise one, two, three, or four TWJ-binding domains. The aptamer containing one or more TWJ-binding domain may be predominantly folded even in the absence of the target due to the multiple Watson-Crick base pairs in its stem. Such aptamer can bind to their target with micro or nano-molar affinity.

CBSA

CBSAs comprise a pair of split aptamer fragments (i.e., a short fragment and a long fragment) with two tandem target-binding domains, which exhibit cooperative binding properties. CBSAs can be engineered from parent split aptamers comprising a single target-binding domain. Advantageously, CBSAs with two target-binding domains exhibit enhanced target response compared with single-domain split aptamers. The first binding event partially stabilizes the CBSA and facilitates the second binding event. This cooperative assembly can reduce the target concentration required to assemble the CBSA several-fold. Thus, CBSAs are highly target-responsive and have superior sensitivity compared to their single-site split aptamer counterparts.

In one embodiment, each piece of the split aptamer according to the present invention may have a minimum length of, for example, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides. Each piece of the split aptamer according to the present invention may have a maximum length of, for example, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleotides. Each piece of the split aptamer according to the present invention may have a length of, for example, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleotides.

In one embodiment, each fragment of CBSA according to the present invention may have a minimum length of, for example, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides. Each fragment of CBSA according to the present invention may have a maximum length of, for example, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleotides. Each fragment of CBSA according to the present invention may have a length of, for example, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleotides.

The CBSAs according to the present invention may comprise at least 10, at least 20, at least 30, at least 40, at least 50, at least 60, at least 70, or at least 80 nucleotides. The CBSAs according to the present invention may comprise at most about 200 nucleotides, at most about 150 nucleotides, at most about 120 nucleotides, at most about 100 nucleotides, at most about 90 nucleotides, at most about 80 nucleotides, at most about 70 nucleotides, at most about 60 nucleotides, or at most about 50 nucleotides. The aptamer according to the present invention comprises, for example, in the range of 10 to 200 nucleotides, preferably 15 to 150 nucleotides, more preferably 20 to 100 nucleotides.

In one embodiment, the CBSA is a cocaine-binding CBSA, including COC-5335 (LF: SEQ ID NO: 8; SF: SEQ ID NO: 9), COC-5334 (LF: SEQ ID NO: 17; SF: SEQ ID NO: 16) and COC-5333 (LF: SEQ ID NO: 34; SF: SEQ ID NO: 35) and sequences sharing at least 50%, 55%, 60%, 65%, 70%, 75%, 80%, 85%, 90%, 95% or 99% identity with COC-5335, COC-5334 and COC-5333.

In another embodiment, the CBSA is a synthetic cathinone-binding CBSA. In a specific embodiment, the CBSA is a MDPV-binding CBSA, MDPV-6335 (LF: SEQ ID NO: 25; SF: SEQ ID NO: 26) and sequences sharing at least 50%, 55%, 60%, 65%, 70%, 75%, 80%, 85%, 90%, 95% or 99% identity with MDPV-6335.

The MDPV-6335 is engineered from an MDPV-binding aptamer (SEQ ID NO: 24) comprising a TWJ binding domain and three stems. The MDPV-binding aptamer binds to MDPV with a $K_D$ of 6 µM. Two different parent split aptamer pairs are derived with a single binding pocket from the MDPV-binding aptamer, in which the GAA loop from stem 3 is removed and the number of base-pairs in all stems is decreased. Stem 1 of one parent split aptamer is then connected to stem 3 of the second parent split aptamer via a single thymine linker on each strand to form a MDPV-binding CBSA, MDPV-6335, comprising a long fragment and a short fragment.

In the absence of MDPV, the two fragments remain separate. When the target is added, the CBSA assembles to form a rigid target-CBSA complex. MDPV-6335 has a binding affinity ($K_{1/2}$, target concentration producing half occupancy) of 140.6 µM with a cooperativity ($n_H$) of 1.8, which shows the high degree of target binding cooperativity.

The aptamers/split aptamers/CBSAs of the present invention may include chemical modifications. The chemical modifications as described herein include a chemical substitution at a sugar position, a phosphate position, and/or a base position of the nucleic acid including, for example, incorporation of a modified nucleotide, incorporation of a capping moiety (e.g., 3' capping), conjugation to a high molecular weight, non-immunogenic compound (e.g., polyethylene glycol (PEG)), conjugation to a lipophilic compound, and substitutions in the phosphate backbone. Base modifications may include 5-position pyrimidine modifications, modifications at exocyclic amines, substitution of 4-thiouridine, substitution of 5-bromo- or 5-iodo-uracil, and backbone modifications. Sugar modifications may include 2'-amine nucleotides (2'-NH2), 2'-fluoronucleotides (2'-F), and 2'-O-methyl (2'-OMe) nucleotides. Such modifications may improve the stability of the aptamers or make the aptamers more resistant to degradation. In some embodiments, each base of a given type (e.g., A, T, C, and G) may contain the same chemical modification.

The aptamers/split aptamers/CBSAs may be modified by addition of one or more reporter labels (or detectable labels). In some embodiments, the label may be attached to either the 5' or 3' end of the aptamer. The label may also be attached with the backbone of the aptamer. The skilled person will be aware of techniques for attaching labels to nucleic acid strands. The detectable label may be attached directly or indirectly to the nucleic acid aptamer. If the label is indirectly attached to the nucleic acid aptamer, it may be by any mechanism known to one of skill in the art, such as using biotin and streptavidin.

The aptamers/split aptamers/CBSAs may comprise a reporter label, such as a fluorescent dye, nanoparticle, or an enzyme. Exemplary labels include, but are not limited to, an organic donor fluorophore or an organic acceptor fluorophore, a luminescent lanthanide, a fluorescent or luminescent nanoparticle, an affinity tag such as biotin, or a polypeptide. In some embodiments, the aptamer may comprise a fluorescent label, for example, fluorescein, TAMRA, rhodamine, Texas Red, Alexa Fluor (e.g., AlexaFluor 488, AlexaFluor 532, AlexaFluor 546, AlexaFluor 594, AlexaFluor 633 and AlexaFluor 647), cyanine dye (e.g., Cy7, Cy7.5, Cy5, Cy5.5 and Cy3), Tye dye (e.g., TYE 563, TYE 665, TYE 705), atto dye (e.g., Atto 594 and Atto 633), Hexachlorofluorescein, FAM (6-carboxyfluroescein), BODIPY FL, OliGreen, 40,6-diamidino-2-phenylindol (DAPI), Hoechst 33,258, malachite green (MG), and FITC. The nanoparticle can be an upconversion nanoparticle. In some embodiments, the fluorophore is selected from the group consisting of fluorophores that emit a blue, green, near red or far red fluorescence.

In one embodiment, the reporter label is a fluorescent dye and quencher pair. In certain embodiments, a fluorophore is conjugated at one end of the short fragment of CBSAs and a quencher at the other end of the short fragment of CBSAs. In the absence of its target, the short fragment of the CBSA is flexible, thereby positioning the fluorophore close to the quencher, and the fluorescence is quenched. Upon target binding, CBSA fragments assemble into a rigid conformation, in which the fluorophore and the quencher are separated and the fluorescence is recovered. The resulting recovery of the fluorescence signal directly reflects the extent of the binding and can be used for detection and quantitative measurement of the target concentration.

The quenchers can be, for example, Dabcyl, DDQ-I, Eclipse, Iowa Black FQ, BHQ-1, QSY-7, BHQ-2, DDQ-II, Iowa Black RQ, QSY-21, or BHQ-3.

It is contemplated that the location of the fluorophore and quencher-conjugated short fragment is such that the proximity of fluorophore and quencher provide maximal quenching in an single-stranded flexible conformation and the fluorophore and quencher in an assembled rigid conformation provide maximal fluorescence of the fluorophore. For optimized detection of fluorescence changes that allows utilization of the CBSAs for target detection, it is desirable that the fluorescence in the quenched conformation is as low as possible and the fluorescence in the unquenched conformation is as high as possible combined with the most rapid interconversion from one conformation to the other.

In one embodiment, the CBSA-target complex may produce a time resolved fluorescence energy transfer (TR-FRET) signal or a signal that can be measured by fluorescence polarization (FP), and/or luminescence.

In one embodiment, the aptamer binds to the small-molecule target with a dissociation constant of, for example, about 1 µM, about 2 µM, about 3 µM, about 4 µM, about 5 µM, about 6 µM, about 7 µM, about 8 µM, about 9 µM, or about 10 µM. In specific examples, The aptamer binds to the small molecule with a dissociation constant between about 0.001 µM and about 1000 µM, between about 0.01 µM and about 500 µM, between about 0.1 µM and about 200 µM, between about 0.5 µM and about 100 µM, between about 1 µM and about 100 µM, between about 1 µM and about 50 µM, between about 1 µM and about 30 µM, between about 1 µM and 20 µM, or between about 1 µM and about 10 µM.

DNAzyme

The DNAzymes are G-quadruplex-structured oligonucleotides that mimic the activity of horseradish peroxidase, and are capable of binding hemin and performing $H_2O_2$-mediated oxidation of colorless small-molecule substrates into colored products. DNAzymes have several desirable characteristics, including their signal-amplifying ability, chemical stability, ease of mass production without any batch-to-batch variation, and the simplicity of incorporating them with different sensing elements.

In one embodiment, the DNAzyme may comprise, for example, at least 1, 2, 3, 4, 5, 6, 7, 8, 9, or 10 GGG repeats. The DNAzyme can be split into two fragments, either in a symmetrical or asymmetrical fashion. As a result, each segment of the split DNAzyme may comprise a same or different number of GGG repeats. For example, a DNAzyme comprising 4 GGG repeats can be symmetrically split into two segments, each of which comprises 2 GGG repeats, resulting in a 2:2 split. Other exemplary split modes include, for example, 1:2, 1:3, 1:4, 1:5, 1:6, 1:7, 1:8, 1:9, 2:2, 2:3, 2:4, 2:5, 2:6, 2:7, 2:8, 3:3, 3:4, 3:5, 3:6, 3:7, 4:4, 4:5, 4:6, 4:3, 4:2, 4:1, 5:5, 5:4, 5:3, 5:2, 5:1, 6:4, 6:3, 6:2, 6:1, 7:3, 7:2, 7:1, 8:2, 8:1, and 9:1.

In one embodiment, the split DNAzyme segments can be reconstituted with hemin when they are brought into close proximity to form a layered G-quadruplex complex that exhibits peroxidase-like activity, catalyzing the oxidation of colorless ABTS into dark green $ABTS^{\bullet+}$ by $H_2O_2$.

In one embodiment, the split DNAzyme further comprises at least one spacer between the guanine triplets or within the GGG repeats. In some embodiments, there may be spacers between every guanine triplet. In a further embodiment, one fragment of the split DNAzyme comprises a sequence of 5'-GXGGYGGG-3' (SEQ ID NO: 36), wherein X and Y are spacers, and X and Y may be missing. The other fragment of the split DNAzyme comprises a sequence of 5'-GGGZGGG-3' (SEQ ID NO: 37), wherein Z is a spacer and Z may be missing.

In one embodiment, the spacer is a nucleotide sequence comprising at least one, at least two, at least three, at least four, at least five, at least six, at least seven or at least eight nucleotides. In a preferred embodiment, the spacer comprises one or two nucleotides. The spacers may be selected from A, C, T, AA, AC, AT, CC, CA, CT, TA, TC, and TT. Preferably, the spacer provides better flexibility for DNAzyme assembly, thereby resulting in higher catalytic activity. A shorter spacer might be preferred due to the formation of a more compact G-quadruplex structure that boosts catalytic activity.

In a specific embodiment, the catalytic activity of the 2:2 split DNAzyme is improved by two-fold via rational mutation and deletion of nucleotides within and between the GGG repeats.

In some embodiments, the spacer X, Y, and Z each independently comprises one or two nucleotides. Preferably, the spacer X is T, Y is A or C, and Z is AC or C.

In specific embodiments, the split DNAzyme comprises a fragment pair from strands A0 and B0, A1 and B0, A2 and B0, or A2 and B1, wherein the fragment from A0 comprises 5'-GTGGAGGGT-3'(SEQ ID NO: 38), the fragment from A1 comprises 5'-GGGAGGGT-3' (SEQ ID NO: 39), the fragment from A2 comprises 5'-GGGCGGGT-3' (SEQ ID NO: 40), the fragment from B0 comprises 5'-AGGGACGGG-3' (SEQ ID NO: 41), and the fragment from B1 comprises 5'-AGGGCGGG-3' (SEQ ID NO: 42).

CBSAzyme

In one embodiment, the subject invention provides a CBSAzyme-based sensor, comprising a pair of split DNAzyme segments and a pair of CBSAs fragments selected to a small-molecule target. In one embodiment, the CBSAzyme-based sensor comprises a pair of highly target-responsive CBSAs and an engineered split DNAzyme with peroxidase-mimicking catalytic activity, wherein the pair of CBSA fragments is coupled to the split DNAzyme segments. The CBSAzyme-based sensor further comprises a signal reporter, which comprises a mixture of a peroxidase substrate and $H_2O_2$.

In one embodiment, the CBSAzyme comprises or consists of two oligonucleotide fragments, each with a CBSA region containing two tandem target-binding domains and a split horseradish-peroxidase-mimicking DNAzyme module. CBSAzymes are ideal sensing elements for small-molecule detection as they inherit the high target responsiveness of CBSAs and the catalytic activity of DNAzymes, which enables label-free, amplified naked-eye detection.

In one embodiment, the CBSAzyme comprises a first fragment (i.e., long fragment) and a second fragment (i.e., short fragment), the first fragment comprising a first segment of the split DNAzyme and a long fragment of the CBSA, the second fragment comprising a second segment of the split DNAzyme and a short fragment of the CBSA.

In one embodiment, the pair of CBSA fragments is coupled to the pair of split DNAzyme segments via nucleotide linkers. The linkers locate between the fragments of the CBSA and the segments of DNAzyme. In a further embodiment, the CBSAzyme comprises a first linker between the long fragment of the CBSA and the first segment of the split DNAzyme, and a second linker between the short fragment of the CBSA and the second segment of the split DNAzyme.

The linkers are nucleotide sequences comprising at least one, at least two, at least three, at least four, at least five, at least six, at least seven or at least eight nucleotides. In a preferred embodiment, the linkers comprise one or two nucleotides. The first and second linkers may have same or different sequences. In a specific embodiment, the linkers are selected from A, C, T, AA, AC, AT, CC, CA, CT, TA, TC, and TT.

In the absence of a small-molecule target, the two fragments of the CBSAzyme remain separate. In the present of the small-molecule target, the two fragments of the CBSA in CBSAzyme effectively assemble, bringing the two DNAzyme segments into close proximity. When hemin is present, the assembled DNAzyme module accommodates hemin within its G-quadruplex, allowing for $H_2O_2$-mediated oxidation of ABTS to ABTS$^{\bullet+}$, thereby rapidly turning the solution from colorless to dark green.

In one embodiment, the CBSAzyme is a selective for cocaine, comprising a CBSA selective for cocaine and a pair of split DNAzyme segments. In a specific embodiment, the CBSA is selected from i) COC-5335 having a long fragment of SEQ ID NO: 8 and a short fragment of SEQ ID NO: 9; ii) COC-5334 having a long fragment of SEQ ID NO: 17 and a short fragment of SEQ ID NO: 16; and iii) COC-5333 a long fragment of SEQ ID NO: 34 and a short fragment of SEQ ID NO: 35. The split DNAzyme comprises segments from strands A2 and B0.

In a specific embodiment, the CBSAzyme is CBSAzyme-5335-22, where the DNAzyme segment from Strand A2 (5'-GGGCGGGT-3') is attached to the 3' terminus of the long fragment of COC-5335 via an A-T dinucleotide linker, and the DNAzyme segment from strand B1 (5'-AGGGCGGG-3') is attached to the 5' terminus of the short fragment of COC-5335 via an A-A dinucleotide linker. In another embodiment, the DNAzyme segment from strand A2 (5'-GGGCGGGT-3') is attached to the 3' terminus of the long fragment of COC-5335 via an A linker. Preferably, CBSAzyme-5335-22 has a long fragment having a sequence of SEQ ID NO: 10 and a short fragment having a sequence of SEQ ID NO: 11.

In the absence of cocaine, these two CBSAzyme fragments are separated and the split DNAzyme remains unassembled and incapable of oxidizing ABTS. Thus, the solution remains clear. In the presence of cocaine, both fragments assemble, bringing the two DNAzyme segments into close proximity. The assembled DNAzyme module accommodates hemin within its G-quadruplex, allowing for $H_2O_2$-mediated oxidation of ABTS to ABTS$^{\bullet+}$, producing a dark green-colored solution, which can be seen by naked eyes.

In one embodiment, the CBSAzyme is CBSAzyme-5334-22, comprising a pair of CBSA fragments, COC-5334, in which one base pair from the termini of the CBSA fragments of COC-5335 closest to the DNAzyme segments is truncated. The DNAzyme segment from strand A2 (5'-GGGCGGGT-3') is attached to the 3' terminus of the long fragment of COC-5334 via an A-T dinucleotide linker, and the DNAzyme segment from strand B1 (5'-AGGGCGGG-3') is attached to the 5' terminus of the short fragment of COC-5334 via an A-A dinucleotide linker. In another embodiment, the DNAzyme segment from strand A2 (5'-GGGCGGGT-3') is attached to the 3' terminus of the long fragment of COC-5334 via an A linker. Preferably, CBSAzyme-5334-22 has a long fragment having a sequence of SEQ ID NO: 12 and a short fragment having a sequence of SEQ ID NO: 13.

In one embodiment, the CBSAzyme is CBSAzyme-5333-22, comprising a pair of CBSA fragments, COC-5333, in which two base pairs from the termini of the CBSA fragments of COC-5335 closest to the DNAzyme segments are truncated. The DNAzyme segment from strand A2 (5'-GGGCGGGT-3') is attached to the 3' terminus of the long fragment of COC-5333 via an A-T dinucleotide linker, and the DNAzyme segment from strand B1 (5'-AGGGCGGG-3') is attached to the 5' terminus of the short fragment of COC-5333 via an A-A dinucleotide linker. In another embodiment, the DNAzyme segment from strand A2 (5'-GGGCGGGT-3') is attached to the 3' terminus of the long fragment of COC-5333 via an A linker. Preferably, CBSAzyme-5333-22 has a long fragment having a sequence of SEQ ID NO: 14 and a short fragment having a sequence of SEQ ID NO: 15.

In one embodiment, the CBSAzyme is CBSAzyme-5334-13, comprising COC-5334, and a split DNAzyme having a 1:3 split mode, in which one segment of the split DNAzyme comprises 1 GGG repeat while the other segment of the split DNAzyme comprises 3 GGG repeats. In a further embodiment, the DNAzyme segment having three GGG repeats is coupled to the short fragment of the CBSA (COC-5334-SF) via an A-A dinucleotide linker. The DNAzyme segment having 1 GGG repeat is coupled to the long fragment of the CBSA (COC-5334-LF) via an A-T dinucleotide linker or an A linker. In a specific embodiment, the DNAzyme segment having three GGG repeats comprises two spacers between the GGG repeats. In a preferred embodiment, the spacers are C and AT.

Advantageously, CBSAzyme-5334-13 demonstrates much lower background assembly relative to CBSAzyme-5334-22 in the absence of cocaine, most likely due to the low stability of 1:3 split DNAzymes. The 1:3 split CBSAzyme also has a higher level of activity in the presence of cocaine relative to the 2:2 split CBSAzyme.

In a preferred embodiment, the CBSAzyme is COC-CBSAzyme (SF: SEQ ID NO: 19 and LF: SEQ ID NO: 20) comprising the A/AA linker combination which favors assembly of both the CBSA and the split DNAzyme.

In some embodiments, the aptamer is specific for cocaine and does not bind to various structurally similar drugs such as benzoylecgonine (BZE), and methylecgonidine (MEG) as well as structurally dissimilar interferent drugs such as nicotine (NIC), and scopolamine (SCP).

In one embodiment, the CBSAzyme is a MDPV-CBSAzyme, comprising a CBSA that binds to MDPV and other synthetic cathinones, and a split DNAzyme. In a specific embodiment, the CBSA is MDPV-6335. The split DNAzyme having a 1:3 split mode, in which one segment of the split DNAzyme comprises 1 GGG repeat while the other segment of the split DNAzyme comprises 3 GGG repeats. In a further embodiment, the DNAzyme segment having three GGG repeats is coupled to the short fragment of MDPV-6335 (MDPV-6335-SF) via an A-A dinucleotide linker. The DNAzyme segment having 1 GGG repeat is coupled to the long fragment of MDPV-6335 (MDPV-6335-LF) via an A linker. In a specific embodiment, the DNAzyme segment having three GGG repeats comprises two spacers between the GGG repeats. In a preferred embodiment, the spacers are C and AT.

In some embodiment, the split DNAzyme comprises segments from strands A0, A1, A2, B1 and B0. For example, the DNAzyme segment from Strand A2 (5'-GGGCGGGT-3') may be attached to the 3' terminus of MDPV-6335-LF via an A-T dinucleotide linker or an A linker, and the DNAzyme segment from Strand B1 (5'-AGGGCGGG-3') maybe attached to the 5' terminus of MDPV-6335-SF via an A-A dinucleotide linker.

Preferable, the MDPV-CBSAzyme has a long fragment having a sequence of SEQ ID NO: 28 or a sequence sharing at least 50%, 55%, 60%, 65%, 70%, 75%, 80%, 85%, 90%, 95% or 99% identity with SEQ ID NO: 28, and a short fragment having a sequence of SEQ ID NO: 29 or a sequence sharing at least 50%, 55%, 60%, 65%, 70%, 75%, 80%, 85%, 90%, 95% or 99% identity with SEQ ID NO: 29.

Advantageously, the MDPV-CBSAzyme retains excellent cross-reactivity to 10 structurally-similar synthetic cathinone analogs including MDPV, methylone, pentylone, 3,4-methylenedioxy-α-pyrrolidinobutiophenone (MDPBP), mephedrone, 4-methyl-α-pyrrolidinobutiophenone (MPBP), 4'-methyl-α-pyrrolidinohexanophenone (MPHP), naphyrone, methedrone, ethylone, and butylone but does not bind to interferents, including common cutting agents and illicit drugs such as caffeine, benzocaine, lidocaine, sucrose and methamphetamine.

Importantly, the stem length of the CBSA is crucial for achieving high signal gain and low background assembly. The split mode of the DNAzyme has a profound impact on CBSAzyme performance, for example, changing the 2:2 split mode to 1:3 results in higher enzymatic activity in the presence of target and lower background signal when the target is absent. The length of the linker also had an effect on signal gain, in which mononucleotide and dinucleotide linkers are optimal for the long and short CBSAzyme fragments, respectively. This particular combination of linkers provides flexibility for DNAzyme assembly with minimal steric hindrance.

In one embodiment, the CBSAzyme, according to the subject invention, is selected from i) COC-CBSAzyme-5335-22 having a first fragment of SEQ ID NO: 10 and a second fragment of SEQ ID NO: 11; ii) COC-CBSAzyme-5334-22 having a first fragment of SEQ ID NO: 12 and a second fragment of SEQ ID NO: 13; iii)) COC-CBSAzyme-5333-22 having a first fragment of SEQ ID NO: 14 and a second fragment of SEQ ID NO: 15; iv) COC-CBSAzyme-5334-13 (AT/AA) having a first fragment of SEQ ID NO: 18 and a second fragment of SEQ ID NO: 19; v) COC-CBSAzyme-5334-13 (A/AA) having a first fragment of SEQ ID NO: 20 and a second fragment of SEQ ID NO: 19; vi) COC-CBSAzyme-5334-13 (A/A) having a first fragment of SEQ ID NO: 20 and a second fragment of SEQ ID NO: 21; and vii) MDPV-CBSAzyme having a first fragment of SEQ ID NO: 28 and a second fragment of SEQ ID NO: 29.

Method of Using CBSAzyme

The subject invention provides methods of using the CBSAzyme-based assays for rapid and naked-eye detection of small-molecule targets in a sample. The method comprises contacting the sample with a CBSAzyme-based sensor selective for the small-molecule target, and detecting the small-molecule target in the sample.

Advantageously, the method utilizes CBSAzymes to achieve sensitive, naked-eye small-molecule detection, a feat that cannot be achieved with any other split-aptamer-DNAzyme conjugates. Because CBSAzymes are entirely based on nucleic acids, with no chemical modifications required, they can be easily synthesized in a cost-effective and reproducible manner. Additionally, the CBSAzymes themselves are chemically stable and resistant to harsh environmental conditions. Moreover, CBSAzyme-based assays require no instrumentation, and are simple to perform—requiring only sample-reagent mixing and visual interpretation.

The CBSAzyme-based sensor comprises a CBSAzyme comprising a pair of CBSA fragments and a split DNAzyme with peroxidase-mimicking catalytic activity. The CBSAzyme comprises two fragments, one of which comprises a long fragment of the CBSA linked to one segment of the split DNAzyme and the other of which comprises a short fragment of the CBSA linked to another segment of the split DNAzyme. The CBSAzyme-based sensor further comprises a signal reporter, which comprises a mixture of a peroxidase substrate and $H_2O_2$.

In the absence of the small-molecule target, the two fragments of the CBSAzyme remain separate and thus the unassembled split DNAzyme module remains inactive and incapable of oxidizing the peroxidase substrate (e.g., ABTS). In the present of the small-molecule target, the two fragments of the CBSA in CBSAzyme effectively assemble, bringing the two DNAzyme segments into close proximity. When hemin is present, the assembled DNAzyme forms the G-quadruplex structure which accommodates hemin, allowing for $H_2O_2$-mediated oxidation of the peroxidase substrate (e.g., from ABTS to $ABTS^{\bullet+}$), thereby rapidly changing the color of the reaction solution (e.g., turning the solution from colorless to dark green). Advantageously, this method provides very low levels of background signal because the fragments only underwent minimal assembly in the absence of target.

The method of the subject invention is remarkably simple, fast and specific. For example, the detection can be performed in a single tube containing the CBSAzyme-based sensor and the sample of interest.

In one embodiment, the subject invention provides a method for rapid, sensitive and visual detection of a small-molecule target in a sample comprising contacting the sample with a CBSAzyme-based sensor comprising a CBSAzyme selective for the small-molecule target, and a signal reporter, the CBSAzyme comprising a pair of CBSA fragments grafted to a pair of split DNAzyme segments, and detecting the small-molecule target in the sample by determining whether a signal occurs upon the small-molecule target binding to the CBSAzyme, the signal being a color change, which is indicative of the presence of the small-molecule target in the sample. The method may further comprise a step of contacting the CBSAzyme-based sensor with a compound that acts as a cofactor of the split DNAzyme.

In certain embodiments, the method for rapid, sensitive and visual detection of a small-molecule target in a sample comprising contacting the sample with a CBSAzyme selective for the small-molecule target, the CBSAzyme comprising a pair of CBSA fragments grafted to a pair of split DNAzyme segments, contacting the sample and CBSAzyme with a compound that acts as a cofactor of the split DNAzyme, adding a signal reporter, and detecting the small molecule in the sample, the detection of the small-molecule target comprising measuring a signal generated from the signal reporter.

In one embodiment, the detection of the small-molecule target comprises measuring a signal generated upon contacting the sample with the CBSAzyme-based sensor. The signal generated upon contacting the sample with the CBSAzyme-based sensor has optical properties that can be detected by naked eyes and quantified by, for example, the absorption.

In another embodiment, the optical properties can be quantified by, for example, a microplate-reader or portable photometer, allowing for high-throughput or on-site detection, respectively.

In one embodiment, the compound/cofactor for promoting the assembly of the split DNAzyme segments is hemin. The signal reporter comprises a mixture of a peroxidase substrate (e.g., ABTS) and $H_2O_2$. The signal generated from the signal reporter is the color change resulted from the $H_2O_2$-mediated oxidation of the peroxidase substrate (e.g., from ABTS to $ABTS^{\bullet+}$) by the peroxidase-mimicking catalytic activity of the split DNAzyme. Thus, a change in color is indicative of the presence of the small-molecule target in the sample. Such change in color can be detected by naked eyes.

In another embodiment, the method further comprises determining the concentration of the small-molecule target in the sample. The determination can comprise comparing the absorption signal generated upon contacting the sample with a CBSAzyme-based sensor with a standard calibration curve of the absorption signal of the ABTS$^{\bullet+}$, for example, at 418 nm in the presence of various concentrations of the small-molecule target.

In one embodiment, the subject invention provides a method for detecting cocaine in a sample wherein said method comprises contacting said sample with a CBSAzyme-based sensor selective for cocaine and detecting cocaine in the sample by determining whether a signal occurs upon cocaine binding to the CBSAzyme, the signal being a color change, which is indicative of the presence of cocaine in the sample. The CBSAzyme-based sensor comprises a CBSAzyme selective for cocaine and a signal reporter being a mixture of a peroxidase substrate and $H_2O_2$, the peroxidase substrate being ABTS.

Because the color intensity of the solution was proportional to the concentration of cocaine, cocaine concentrations as low as 10 µM can be detected by naked eye within 5 minutes. A calibration curve using the absorbance ABTS$^{\bullet+}$ at 418 nm after 15 minutes of reaction can be used for determining the concentration of cocaine and a detection limit of 1 µM cocaine with a linear range from 0 to 100 µM is observed. The method can achieve successful cocaine detection in a biological sample including body fluids such as saliva and urine.

In specific embodiments, the CBSAzyme-based sensor comprises a CBSAzyme selected from i) COC-CBSAzyme-5335-22 having a first fragment of SEQ ID NO: 10 and a second fragment of SEQ ID NO: 11; ii) COC-CBSAzyme-5334-22 having a first fragment of SEQ ID NO: 12 and a second fragment of SEQ ID NO: 13; iii)) COC-CBSAzyme-5333-22 having a first fragment of SEQ ID NO: 14 and a second fragment of SEQ ID NO: 15; iv) COC-CBSAzyme-5334-13 (AT/AA) having a first fragment of SEQ ID NO: 18 and a second fragment of SEQ ID NO: 19; v) COC-CBSAzyme-5334-13 (A/AA) having a first fragment of SEQ ID NO: 20 and a second fragment of SEQ ID NO: 19; vi) COC-CBSAzyme-5334-13 (A/A) having a first fragment of SEQ ID NO: 20 and a second fragment of SEQ ID NO: 21. Preferably, the CBSAzyme is COC-CBSAzyme-5334-13 (A/AA) having a first fragment of SEQ ID NO: 20 and a second fragment of SEQ ID NO: 19.

Advantageously, the method according to the subject invention can be used to specifically detect cocaine and does not respond to other interferent drugs because the CBSAzyme does not cross-react to scopolamine and sucrose and shows only minimal cross-reactivity for caffeine, chlorpromazine, promazine, and levamisole, and moderate cross-reactivity for diphenhydramine and lidocaine.

In one embodiment, the subject invention provides a method for detecting a synthetic cathinone in a sample wherein said method comprises contacting said sample with a CBSAzyme-based sensor comprising a CBSAzyme selective for the synthetic cathinone and determining whether a change in color occurs, wherein a change in color is indicative of the presence of synthetic cathinone in the sample. Such change in color can be detected by naked eyes.

In a specific embodiment, the CBSAzyme-based sensor comprises a CBSAzyme being MDPV-CBSAzyme having a first fragment of SEQ ID NO: 28 and a second fragment of SEQ ID NO: 29.

In a further embodiment, the subject invention provides a method for detecting MDPV in a sample wherein said method comprises contacting said sample with the CBSAzyme-based sensor that binds MDPV and determining whether a change in color occurs, wherein a change in color is indicative of the presence of MDPV in the sample.

Because the color intensity of the solution was proportional to the concentration of MDPV, MDPV concentrations as low as 30 µM can be detected by naked eye within 5 minutes. A calibration curve using the absorbance ABTS$^{\bullet+}$ at 418 nm after 15 minutes of reaction can be used for determining the concentration of MDPV and a detection limit of 3 µM MDPV with a linear range from 0 to 100 µM is observed.

In one embodiment, the method according to the subject invention allow the visual detection of a variety of synthetic cathinones including, MDPV, methylone, pentylone, 3,4-methylenedioxy-α-pyrrolidinobutiophenone (MDPBP), mephedrone, 4-methyl-α-pyrrolidinobutiophenone (MPBP), 4'-methyl-α-pyrrolidinohexanophenone (MPHP), naphyrone, methedrone, ethylone, and butylone.

Advantageously, the CBSAzyme-based assay retained excellent specificity against interferents, including common cutting agents and illicit drugs such as caffeine, benzocaine, lidocaine, sucrose and methamphetamine.

In one embodiment, the subject invention provide a method for visually detecting one or more synthetic cathinones in a sample, the method comprising contacting the sample with a CBSAzyme-based sensor comprising a signal reporter and a CBSAzyme that binds to one or more synthetic cathinones, and detecting one or more synthetic cathinones in the sample by determining whether a signal occurs upon one or more synthetic cathinones binding to the CBSAzyme, the signal being a color change, which is indicative of the presence of one or more synthetic cathinones in the sample.

In one embodiment, the method according to the subject invention can achieve superior sensitivity for target detection at low micromolar or nanomolar concentration, for example, as low as about 200 µM, about 150 µM, about 100 µM, about 10 µM, about 1 µM.

In one embodiment, the methods for small molecule detection provided herein are rapid and can be completed in about 5 minutes to about 120 minutes, about 6 minutes to about 110 minutes, about 7 minutes to about 100 minutes, about 8 minutes to about 90 minutes, about 9 minutes to about 80 minutes, about 10 minutes to about 70 minutes about 15 minutes to about 60 minutes, about 20 minutes to about 50 minutes, or about 25 minutes to about 40 minutes. In some embodiments, the method can be completed in about 5 minutes, about 10 minutes, about 15 minutes, about 20 minutes, about 25 minutes, about 30 minutes, about 35 minutes, about 40 minutes, about 45 minutes, about 50 minutes, about 55 minutes, about 60 minutes, about 65 minutes, about 70 minutes, about 75 minutes, about 80 minutes, about 85 minutes, about 90 minutes, about 95 minutes, about 100 minutes, about 105 minutes, about 110 minutes, about 115 minutes, or about 120 minutes.

In another embodiment, the methods for small molecule detection provided herein are rapid and can be completed in about 5 seconds to about 5 minutes, about 10 seconds to about 4 minutes, about 15 seconds to about 3 minutes, about 20 seconds to about 2 minutes, or about 25 seconds to about 1 minute.

In one embodiment, the subject invention provides a method for detecting small molecules that are biomarkers for diagnosis of a disease or condition, or monitoring therapeutic response to specific treatments. In specific embodiments, the condition can be, for example, cancer, an injury, an inflammatory disease or a neurodegenerative disease. In some embodiments, the condition can be substance abuse, psychosis, schizophrenia, Parkinson's disease, attention deficit hyperactivity disorder (ADHD), and pain. In some embodiments, the pain is acute pain or chronic pain. In some embodiments, the pain is neuropathic pain, e.g., chronic neuropathic pain.

In one embodiment, the subject invention provides a kit for detecting a small-molecule target, comprising the CBSAzyme-based sensor. The kit can further comprise instructions for using the kit. In some embodiments, the kit may comprise other reagents suitable for detecting the small-molecule target. The reagents may include ABTS, $H_2O_2$, hemin, and stabilizing agents.

In one embodiment, the methods, assays and products according to the subject invention can be used for the sensitive and accurate detection of small-molecule targets in fields including environmental monitoring, food safety, law enforcement, medical diagnostics, and public health.

The subject invention encompasses the use of sequences having a degree of sequence identity with the nucleic acid sequence(s) of the present invention. A similar sequence is taken to include a nucleotide sequence which may be at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to the subject sequence. Typically, the similar sequences will comprise the same or similar secondary structure as the subject nucleic acid aptamer. In one embodiment, a similar sequence is taken to include a nucleotide sequence which has one or several additions, deletions and/or substitutions compared with the subject sequence.

The term "about" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 0-20%, 0 to 10%, 0 to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed. In the context of compositions containing amounts of ingredients where the term "about" is used, these compositions contain the stated amount of the ingredient with a variation (error range) of 0-10% around the value (X±10%).

EXAMPLES

Experimental Section

Materials and Methods

Materials.

2,2'-azinobis(3-ethylbenzothiazoline)-6-sulfonic acid (ABTS), benzocaine, caffeine, chlorpromazine HCl, cocaine HCl, diphenhydramine HCl, levamisole HCl, lidocaine HCl, methamphetamine HCl, promazine HCl, scopolamine HCl, and sucrose were purchased from Sigma-Aldrich. Hemin was purchased from Frontier Scientific and prepared as a 5 mM stock solution in dimethyl sulfoxide (DMSO) and stored at −20° C. before use. 30% hydrogen peroxide ($H_2O_2$) was purchased form Fisher Scientific. Butylone, ethylone, 3,4-methylenedioxy-α-pyrrolidinobutiophenone, 3,4-methylenedioxypyrovalerone, mephedrone, methedrone, methylone, 4-methyl-α-pyrrolidinobutiophenone, 4'-methyl-α-pyrrolidinohexanophenone, naphyrone, and pentylone were purchased from Cayman Chemical. All synthetic cathinones were purchased as hydrochloride salts. All other chemicals were purchased from Sigma-Aldrich unless otherwise specified. All DNA oligonucleotides were purchased from Integrated DNA Technologies. Oligonucleotides were dissolved in PCR grade water and DNA concentrations were measured with a NanoDrop 2000 (Thermo Scientific). The names and sequences of the DNA oligonucleotides (5'-3') are listed below, where X, Y and Z indicate selected modification sites within the spacers between GGG repeats; /5IAbRQ/ represents IowaBlack RQ quencher; /3Cy5Sp/ represents Cy5 fluorophore.

```
Strand A:
                                          (SEQ ID NO: 1)
5'-AGT AAC AAC AAT CAA AAT ATG XGG YGG GT-3'

Strand A0:
                                          (SEQ ID NO: 2)
5'-AGT AAC AAC AAT CAA AAT ATG TGG AGG GT-3'

Strand A1:
                                          (SEQ ID NO: 3)
5'-AGT AAC AAC AAT CAA AAT ATG GGA GGG T-3'

Strand A2:
                                          (SEQ ID NO: 4)
5'-AGT AAC AAC AAT CAA AAT ATG GGC GGG T-3'

Strand B:
                                          (SEQ ID NO: 5)
5'-AGG GZG GGA AAT TTT GAT TGT TGT TAC T-3'

Strand B0:
                                          (SEQ ID NO: 6)
5'-AGG GAC GGG AAA TTT TGA TTG TTG TTA CT-3'

Strand B1:
                                          (SEQ ID NO: 7)
5'-AGG GCG GGA AAT TTT GAT TGT TGT TAC T-3'

COC-5335-LF:
                                          (SEQ ID NO: 8)
5'-CTC TTT CAA CGA AGT GGG TCT CCT TCA ACG AAG
TGG GTC TC-3'

COC-5335-SF:
                                          (SEQ ID NO: 9)
5'-GA GAC AAG GTG ACA AGG AG-3'

COC-CBSAzyme-5335-22-LF:
                                          (SEQ ID NO: 10)
5'-CTC TTT CAA CGA AGT GGG TCT CCT TCA ACG AAG
TGG GTC TCA TGG GCG GGT-3'

COC-CBSAzyme-5335-22-SF:
                                          (SEQ ID NO: 11)
5'-AGG GCG GGA AGA GAC AAG GTG ACA AGG AG-3'

COC-CBSAzyme-5334-22-LF:
                                          (SEQ ID NO: 12)
5'-CTC TTT CAA CGA AGT GGG TCT CCT TCA ACG AAG
TGG GTC TAT GGG CGG GT-3'

COC-CBSAzyme-5334-22-SF:
                                          (SEQ ID NO: 13)
5'-AGG GCG GGA AAG ACA AGG TGA CAA GGA G-3'
```

COC-CBSAzyme-5333-22-LF:
(SEQ ID NO: 14)
5'-CTC CTT CAA CGA AGT GGG TCT CCT TCA ACG AAG TGG GTC ATG GGC GGG T-3'

COC-CBSAzyme-5333-22-SF:
(SEQ ID NO: 15)
5'-AGG GCG GGA AGA CAA GGT GAC AAG GAG-3'

COC-5334-SF:
(SEQ ID NO: 16)
5'-AG ACA AGG TGA CAA GGA G-3'

COC-5334-LF:
(SEQ ID NO: 17)
5'-CTC CTT CAA CGA AGT GGG TCT CCT TCA ACG AAG TGG GTC-3'

COC-CBSAzyme-5334-13-LF (AT linker):
(SEQ ID NO: 18)
5'-CTC CTT CAA CGA AGT GGG TCT CCT TCA ACG AAG TGG GTC TAT GGG-3'

COC-CBSAzyme-5334-13-SF (AA linker):
(SEQ ID NO: 19)
5'-GGG TAG GGC GGG AAA GAC AAG GTG ACA AGG AG-3'

COC-CBSAzyme-5334-13-LF (A linker):
(SEQ ID NO: 20)
5'-CTC CTT CAA CGA AGT GGG TCT CCT TCA ACG AAG TGG GTC TAG GG-3'

COC-CBSAzyme-5334-13-SF (A linker):
(SEQ ID NO: 21)
5'-GGG TAG GGC GGG AAG ACA AGG TGA CAA GGA G-3'

SAzyme-334-LF:
(SEQ ID NO: 22)
5'-GTC TCC TTC AAC GAA GTG GGT CTA GGG-3'

SAzyme-334-SF:
(SEQ ID NO: 23)
5'-GGG TAG GGC GGG AAA GAC AAG GTG AC-3'

MDPV-Binding Aptamer:
(SEQ ID NO: 24)
5'-CTT ACG ACT CAG GCA TTT TGC CGG GTA ACG AAG TTA CTG TCG TAA G-3'

MDPV-6335-LF:
(SEQ ID NO: 25)
5'-TAC GAC TCA GGC TTT GCC GGG TAT GAC TCA GGC TTT GCC GGG TAA C-3'

MDPV-6335-SF:
(SEQ ID NO: 26)
5'-G TTA CTG TCT TAC TGT CGT A-3'

MDPV-6335-SF-FQ:
(SEQ ID NO: 27)
5'/5IAbRQ/G TTA CTG TCT TAC TGT CGT A/3Cy5Sp/-3'

MDPV-CBSAzyme-LF:
(SEQ ID NO: 28)
5'-TAC GAC TCA GGC TTT GCC GGG TAT GAC TCA GGC TTT GCC GGG TAA CAG GG-3'

MDPV-CBSAzyme-SF:
(SEQ ID NO: 29)
5'-GGG TAG GGC GGG AAG TTA CTG TCT TAC TGT CGT A-3'

LF of parent split MDPV aptamer (1):
(SEQ ID NO: 30)
5'-TAC GAC TCA GGC TTT GCC GGG TA-3'

SF of parent split MDPV aptamer (1):
(SEQ ID NO: 31)
5'-T ACT GTC GTA-3'

LF of parent split MDPV aptamer (2):
(SEQ ID NO: 32)
5'-GAC TCA GGC TTT GCC GGG TAA C-3'

SF of parent split MDPV aptamer (2):
(SEQ ID NO: 33)
5'-GTT ACT GTC-3'

COC-5333-LF:
(SEQ ID NO: 34)
5'-CTC CTT CAA CGA AGT GGG TCT CCT TCA ACG AAG TGG GTC-3'

COC-5333 SF:
(SEQ ID NO: 35)
5'-GAC AAG GTG ACA AGG AG-3'

Segment 1 of 2:2 split DNAzyme:
(SEQ ID NO: 36)
5'-GXGGYGGG-3'

Segment 2 of 2:2 split DNAzyme:
(SEQ ID NO: 37)
5'-GGGZGGG-3'

Split DNAzyme segment from A0:
(SEQ ID NO: 38)
5'-GTGGAGGGT-3'

Split DNAzyme segment from A1:
(SEQ ID NO: 39)
5'-GGGAGGGT-3'

Split DNAzyme segment from A2:
(SEQ ID NO: 40)
5'-GGGCGGGT-3'

Split DNAzyme segment from B0:
(SEQ ID NO: 41)
5'-AGGGACGGG-3'

Split DNAzyme segment from B1:
(SEQ ID NO: 42)
5'-AGGGCGGG-3'.

DNAzyme:
(SEQ ID NO: 43)
5'-GGG CGG GTA GGG CGG G-3'

Segment 1 of 1:3 split DNAzyme:
(SEQ ID NO: 44)
5'-GGG-3'

Segment 2 of 1:3 split DNAzyme:
(SEQ ID NO: 45)
5'-GGG TAG GGC GGG-3'

Determination of Split DNAzyme Activity Utilizing Duplex DNA.

Duplex-DNA-DNAzyme conjugates were prepared by mixing strands A0 and B0, A1 and B0, A2 and B0, or A2 and B1 (0.25 µM final concentration for each strand) in 40 mM HEPES buffer (pH 7.0) containing 50 mM KCl, 0.05% (v/v) Triton X-100, and 1% (v/v) DMSO. Freshly prepared hemin was then added to a final concentration of 1 µM, and the solution was incubated for 30 minutes at room temperature. The mixture was then added to a 384-well plate, and $H_2O_2$ (final concentration 2 mM) and ABTS (final concentration 1.5 mM) were added to initiate the reaction. The absorption intensity at $\lambda=418$ nm (ABTS$^{\bullet+}$) was recorded every minute using a Tecan Infinite M1000 PRO microplate reader. The concentration of ABTS$^{\bullet+}$ was calculated based on the extinction coefficient of ABTS$^{\bullet+}$ at $\lambda=418$ nm ($\varepsilon=36000$ $M^{-1}$ $cm^{-1}$). The concentration of ABTS$^{\bullet+}$ was plotted as a function of time and the initial reaction rates ($V_0$) were determined by calculating the slope of the linear portion of the plot. This parameter was used to evaluate the catalytic activity of the split DNAzymes.

Optimization of KCl and NaCl Concentration.

To maximize the signal gain from the CBSAzymes, the buffer concentrations of KCl and NaCl were optimized using a two-factor, 12-level uniform design. A combination of 12 different KCl and NaCl concentrations was tested. 5 µL of varying concentrations of 10× KCl and NaCl were mixed with 4 µL of HEPES buffer (final concentration: 40 mM, pH 7.0), 13 µL of deionized water (DI), and 2.5 µL of each CBSAzyme fragment (final concentration of each strand: 1 µM). 5 µL of cocaine or MDPV (final concentration: 250 µM) was then added to the mixture and the solution was incubated for 30 minutes. Afterwards, 0.5 µL hemin (final concentration 1 µM) and 2.5 µL Triton X-100 (final concentration 0.05%) were added to the mixture, and the solution was incubated for another 30 minutes. The solution was subsequently transferred into a well of a 384-well plate and then a 10 µL of a substrate solution (final concentrations: 2 mM $H_2O_2$, 1.5 mM ABTS and 40 mM HEPES) was added. The absorbance at 418 nm was monitored every minute using a Tecan Infinite M1000 PRO microplate reader. The combination of salt concentrations that achieved the highest signal gain was used for subsequent experiments.

Determination of CBSAzyme Kinetics.

The following experiments were performed at room temperature. The Michaelis-Menten constant ($K_M$) and turnover number ($k_{cat}$) of the CBSAzyme were determined by varying the concentration of ABTS. Specifically, 1 µM of each fragment was mixed with 250 µM cocaine in 40 mM HEPES (pH 7.0) containing 0.05% Triton X-100, 1% DMSO and optimal concentrations of KCl and NaCl as determined above. This mixture was incubated for 30 minutes and then 1 µM hemin was added. After 30 minutes of incubation, the sample was loaded into a well of a 384-well microplate and the enzymatic reaction was initiated by the addition of 2 mM $H_2O_2$ and various concentrations of ABTS (final concentration: 0.1, 0.5, 1.0, 1.5, 2.0, 4.0, or 6.0 mM). The absorbance at 418 nm was monitored every minute using a Tecan Infinite M1000 PRO microplate reader and the corresponding absorbance values were converted to concentration using the extinction coefficient of ABTS$^{\bullet+}$ at %=418 nm ($\varepsilon$=36000 M$^{-1}$ cm$^{-1}$). The concentration of ABTS$^{\bullet+}$ was plotted against time, and the initial reaction rates were determined by calculating the slope of the linear portion of the plot. To determine $K_M$ and maximal velocity ($V_{max}$), the initial reaction rate was plotted against the concentration of ABTS, and that plot was fitted with the Michaelis-Menten equation[28] using nonlinear regression.

Colorimetric Detection of Cocaine.

Detection was performed by incubating cocaine (final concentrations: 0, 0.1, 0.3, 1, 3, 10, 30, 100, 300, or 1,000 µM) with 1 µM each of COC-CBSAzyme-SF and COC-CBSAzyme-LF in 40 mM HEPES (pH 7.0) with 1 µM hemin, 1 mM KCl, 30 mM NaCl, 0.05% Triton X-100, and 1% DMSO for 15 minutes at room temperature. The sample was then loaded into a well of a 384-well microplate, and the enzymatic reaction was initiated by the addition of 2 mM $H_2O_2$ and 1.5 mM ABTS (final concentrations). The absorbance at 418 nm was monitored every minute using a Tecan Infinite M1000 PRO microplate reader.

Fluorescence Assay for MDPV.

The long fragment and fluorophore-quencher-modified short fragment of MDPV-6335 (final concentration of each: 1 µM) was mixed with 40 mM HEPES buffer (pH 7.0) containing 7 mM KCl and 77 mM NaCl. Various concentrations of MDPV (final concentrations: 1, 3, 10, 30, 100, 300, 1000, or 3000 µM) were added into the mixture, and the solution was incubated for 30 minutes at room temperature. The total reaction volume was 100 µL. Each reaction was loaded into a well of a 96-well microplate and the fluorescence intensity at 668 nm was measured using a Tecan Infinite M1000 PRO microplate reader with excitation at 648 nm. The signal gain was calculated by (F−F$_0$)/F$_0$×100%, where F$_0$ is the fluorescence of MDPV-6335 mixture without MDPV, and F is the fluorescence of MDPV-6335 mixtures with different concentration of MDPV. Signal gain was plotted against the employed MDPV concentration, and the plot was fitted with the Hill equation using Origin 2017 software to calculate the Hill coefficient ($n_H$) and MDPV concentration producing half occupancy ($K_{1/2}$).

Colorimetric Detection of MDPV.

Briefly, 1 µM each of MDPV-CBSAzyme-SF and MDPV-CBSAzyme-LF were incubated with MDPV (final concentrations: 0, 0.1, 0.3, 1, 3, 10, 30, 100, 300, 1,000 µM) in 40 mM HEPES (pH 7.0) with 1 µM hemin, 7 mM KCl, 77 mM NaCl, 0.05% Triton X-100, and 1% DMSO. This mixture was incubated for 15 minutes at room temperature. The sample was then loaded into a well of a 384-well microplate and the enzymatic reaction was initiated by the addition of 2 mM $H_2O_2$ and 1.5 mM ABTS (final concentrations). The absorbance at 418 nm was monitored every minute using a Tecan Infinite M1000 PRO microplate reader.

Circular Dichroism Measurements.

Circular dichroism experiments, including sample preparation, were performed at room temperature. For cocaine, 1 µM of each CBSAzyme fragment was incubated with or without 250 µM cocaine in 40 mM HEPES buffer (pH 7.0) containing 1% DMSO, and optimal KCl and NaCl concentrations (listed under respective circular dichroism figures in ESI) for 30 minutes. Hemin (final concentration 1 µM) or DMSO (for control experiments, final concentration 1% (v/v) for control experiments) was added, and the solution was incubated for another 30 minutes. The samples (300 µL) were transferred into a 1 cm quartz cuvette (Hellma Analytics) to perform circular dichroism measurements using a Jasco J-815 circular dichroism spectropolarimeter with scan range: 235 to 300 nm, scanning speed: 50 nm/min, sensitivity: 100 mdeg, response time: 1 s, bandwidth: 1 nm, total scans: 6. For MDPV, hemin (final concentration 1 µM) or DMSO (for control experiments, final concentration 1% (v/v)) was added to 1 µM of each MDPV-CBSAzyme fragment with or without 200 µM MDPV in 40 mM HEPES buffer (pH 7.0) containing 1% DMSO, 7 mM KCl, and 77 mM NaCl. The mixture was incubated overnight at room temperature. The circular dichroism spectra were recorded with scan range: 220 to 300 nm, scanning speed: 50 nm/min, sensitivity: 5 mdeg, response time: 8 s, bandwidth: 1 nm, total scans: 6. For data analysis, all circular dichroism spectra were averaged and then corrected by subtracting the circular dichroism spectra of the reaction buffer with or without drug.

Example 1—Engineering a Split DNAzyme with High Activity

Peroxidase-mimicking DNAzymes are G-quadruplex-structured oligonucleotides that can perform a catalytic reaction similar to that of horseradish peroxidase. These DNAzymes can be split into two fragments, either in a symmetrical or asymmetrical fashion. For example, Willner et al. have split a single-stranded DNAzyme into two symmetrical segments, with each strand containing two GGG repeats. This is known as the 2:2 split mode. The split DNAzyme segments can be reconstituted with hemin when they are brought into close proximity to form a layered G-quadruplex complex that exhibits peroxidase-like activity, catalyzing the oxidation of colorless 2,2'-azinobis(3-ethylbenzothiazoline)-6-sulfonic acid (ABTS) into dark green ABTS$^{•+}$ by $H_2O_2$. However, the catalytic activity of this split DNAzyme is low. Its activity could be improved by altering the spacers between the guanine triplets.

Figure 1B:
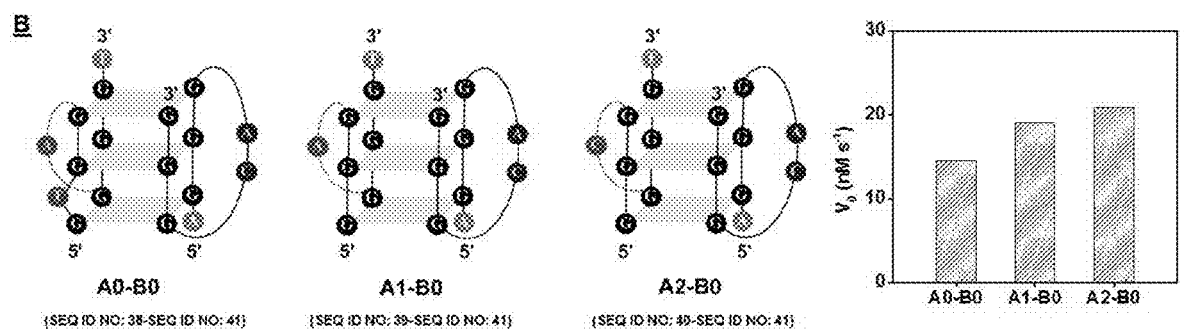
Figure 1C:
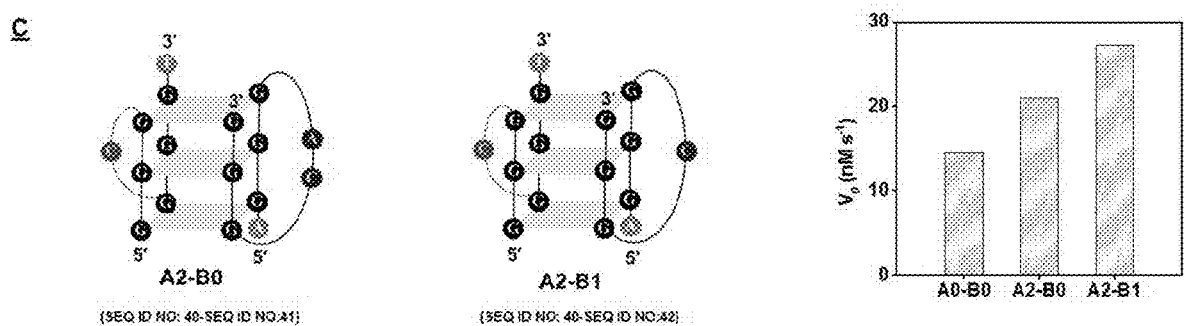
Figure 2A:
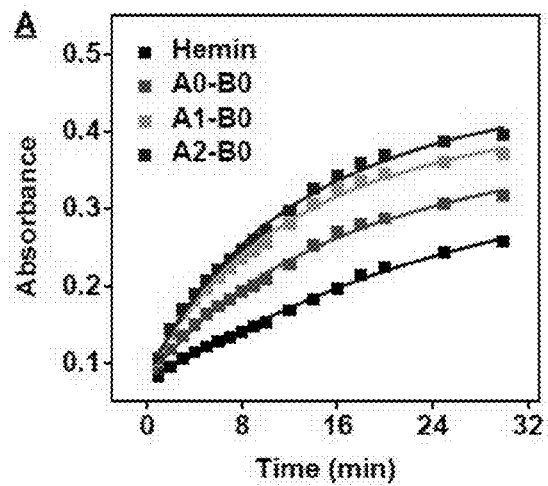
FIGS. 2A-2B show the optimization of the catalytic activity of an assembled split DNAzyme tethered to a DNA duplex. Time-course measurement of absorbance at 418 nm using split DNAzymes with (2A) strand B0 and different variants of strand A and (2B) strand A2 and different variants of strand B. Hemin alone was used as a control.
Figure 2B:
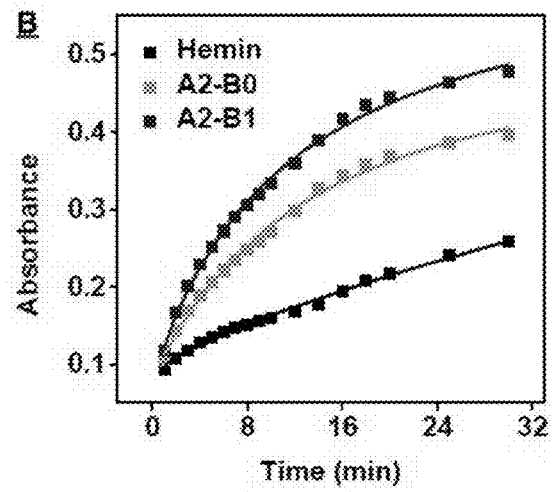

To test this hypothesis, pairs of duplex DNA-DNAzyme conjugates were designed with each fragment containing one segment of the 2:2 split DNAzyme (FIG. 1A), the activity of the original split DNAzyme was first tested (FIG. 1B, A0-B0) using the rate of ABTS$^{•+}$ produced as a benchmark. A reaction rate of 14.5 nM/s was observed for this native split DNAzyme (FIG. 1B). A derivative of strand A0 was then synthesized by removing the thymine at position X to generate strand A1. The assembled A1-B0 split DNAzyme had a higher reaction rate (19.0 nM/s) (FIG. 2A) than the original split DNAzyme (FIG. 1B). This indicated that the thymine bulge originally present within the GGG repeat may be disruptive to the assembly of the split DNAzyme. The adenine at position Y in strand A1 was further replaced with the less bulky cytosine to generate strand A2, and the reaction rate of the assembled A2-B0 split DNAzyme (FIG. 1B) further increased to 20.9 nM/s (FIG. 2A). This improvement in activity may be attributed to the lower steric hindrance produced by cytosine relative to adenine, which provides better flexibility for DNAzyme assembly and thus results in higher catalytic activity. Finally, a derivative of strand B0 was synthesized, in which the adenine at position Z was removed from the adenine-cytosine spacer to form strand B1. The assembled A2-B1 split DNAzyme (FIG. 1C) had a much higher activity (27.3 nM/s) compared to A2-B0 (FIG. 2B). These results showed that shorter spacers promoted formation of a more compact G-quadruplex structure that boosts catalytic activity.

Example 2—Designing CBSA-DNAzyme Conjugates

Figure 3A:
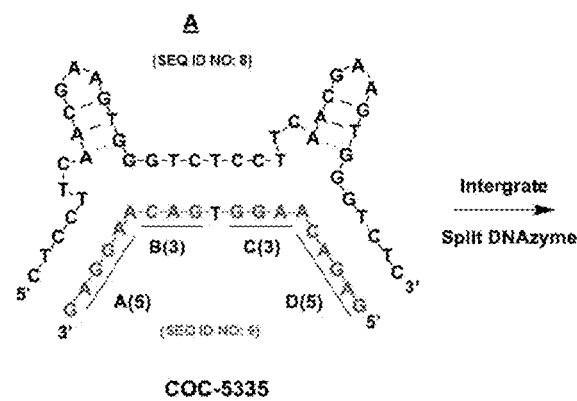
FIGS. 3A-3B show the strategy for engineering the cocaine-binding CBSAzyme from a cocaine-binding CBSA. The split DNAzyme segments from strands A2 and B1 are conjugated to the ends of COC-5335 (LF: SEQ ID NO: 8; SF: SEQ ID NO: 9) (3A) to generate CBSAzyme-5335-22 (LF: SEQ ID NO: 10; SF: SEQ ID NO: 11) (3B).

A cocaine-binding CBSA (COC-5335) (FIG. 3A) containing two binding sites has been previously described. The cocaine-binding CBSA (COC-5335) was far more responsive to its target than its parent split aptamer with a single binding domain. Using this CBSA, ultra-sensitive, one-step detection of cocaine was achieved within fifteen minutes. A CBSA-DNAzyme conjugate was developed for rapid naked-eye cocaine detection using COC-5335 and the optimized split DNAzyme studied above.

Figure 3B:
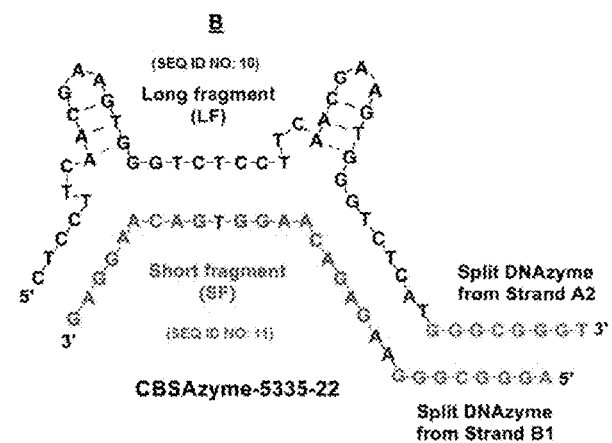
Figure 4:
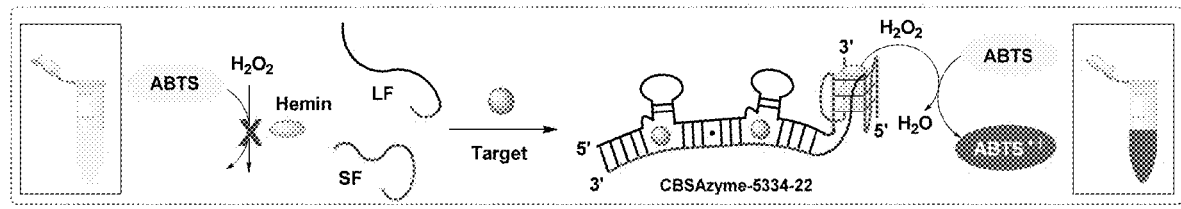
FIG. 4 shows the working principle of colorimetric small-molecule detection based on target-induced CBSAzyme assembly and oxidation of colorless ABTS (left) to produce green-colored ABTS$^{\bullet+}$ (right). The black- and red-colored segments are the long and short fragments of the CBSAzyme, respectively, while blue- and pink-colored segments represent the linker and split DNAzyme segments, respectively.

Specifically, the DNAzyme segment from Strand A2 (5'-GGGCGGGT-3') to the 3' terminus of the long fragment of COC-5335 was attached via an A-T dinucleotide linker, and the DNAzyme segment from Strand B1 (5'-AGGGCGGG-3') to the 5' terminus of the short fragment of COC-5335 was attached via an A-A dinucleotide linker (FIG. 3B). This conjugate was termed CBSAzyme-5335-22. In the absence of cocaine, these two CBSAzyme fragments are separated and the split DNAzyme remains unassembled and incapable of oxidizing ABTS; thus, the solution remains clear (FIG. 4, left). In the presence of cocaine, both fragments assemble, bringing the two DNAzyme segments into close proximity. The assembled DNAzyme module accommodates hemin within its G-quadruplex, allowing for $H_2O_2$-mediated oxidation of ABTS to ABTS$^{•+}$, thereby rapidly turning the solution from clear to dark green (FIG. 4, right).

Figures 5A, 5B, 5C:
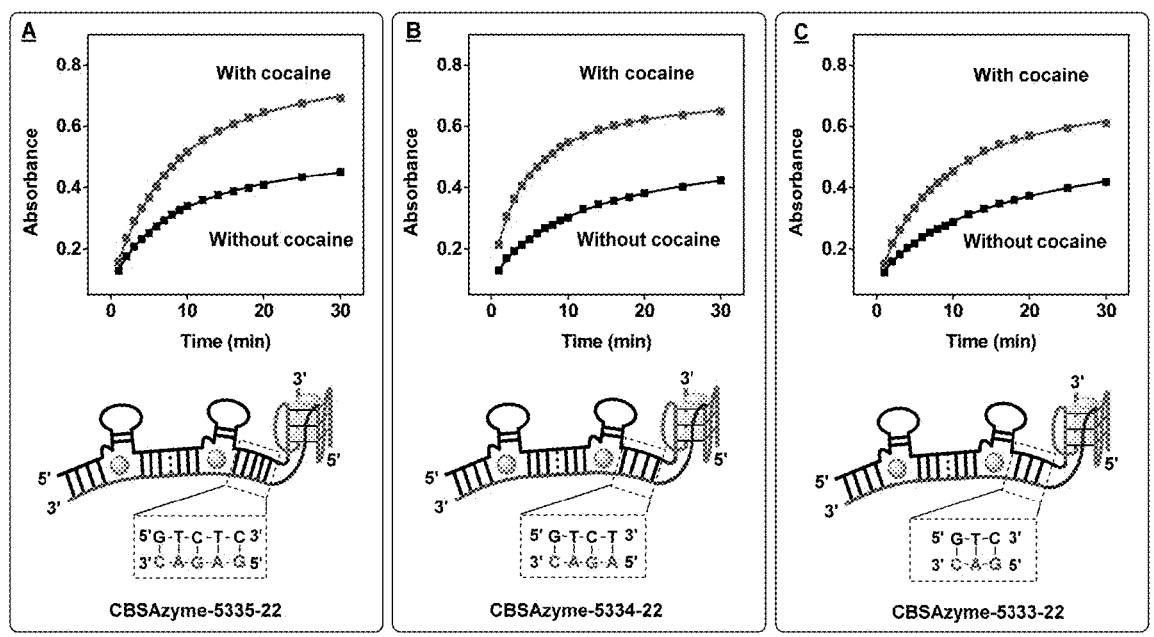
FIGS. 5A-5C show the effect of CBSA stem-length on the performance of the cocaine-detecting CBSAzyme. Time-course of absorbance measurements for (5A) CBSAzyme-5335-22 (LF: SEQ ID NO: 10; SF: SEQ ID NO: 11), (5B) CBSAzyme-5334-22 (LF: SEQ ID NO:12; SF: SEQ ID NO: 13), and (5C) CBSAzyme-5333-22 (LF: SEQ ID NO:14; SF: SEQ ID NO: 15) in the presence and absence of 250 μM cocaine. [Each fragment]=0.25 μM

Example 3—Effect of CBSA Stem Length on CBSAzyme Performance 250 nM of the short and long fragments of CBSAzyme-5335-22 were mixed in reaction buffer in the presence or absence of 250 µM cocaine. After 10 minutes, the absorption of ABTS$^{•+}$ at 418 nm greatly increased in the presence of cocaine. In contrast, the absorbance intensity only slightly increased in the absence of cocaine, most likely due to nonspecific background assembly of the CBSAzyme (FIG. 5A).

To evaluate whether reducing thermostability can mitigate background assembly of the CBSAzyme and improve signal gain, derivatives of CBSAzyme-5335-22 were synthesized by truncating one or two base pairs from the termini of the CBSA fragments closest to the DNAzyme segments to generate CBSAzyme-5334-22 and CBSAzyme-5333-22, respectively. The performance of these derivatives was then tested under their optimized reaction conditions. CBSAzyme-5334-22 achieved lower background assembly while maintaining excellent catalytic activity (FIG. 5B), producing a higher signal gain than CBSAzyme-5335-22. CBSAzyme-5333-22 (FIG. 5C) showed slightly decreased activity while having the same background signal as CBSAzyme-5334-22, demonstrating that further decreases in the thermostability of the CBSAzyme are deleterious for assay performance. CBSAzyme-5334-22 was used for subsequent experiments.

Example 4—Effects of the DNAzyme Split Mode on CBSAzyme Performance

Figure 6A:
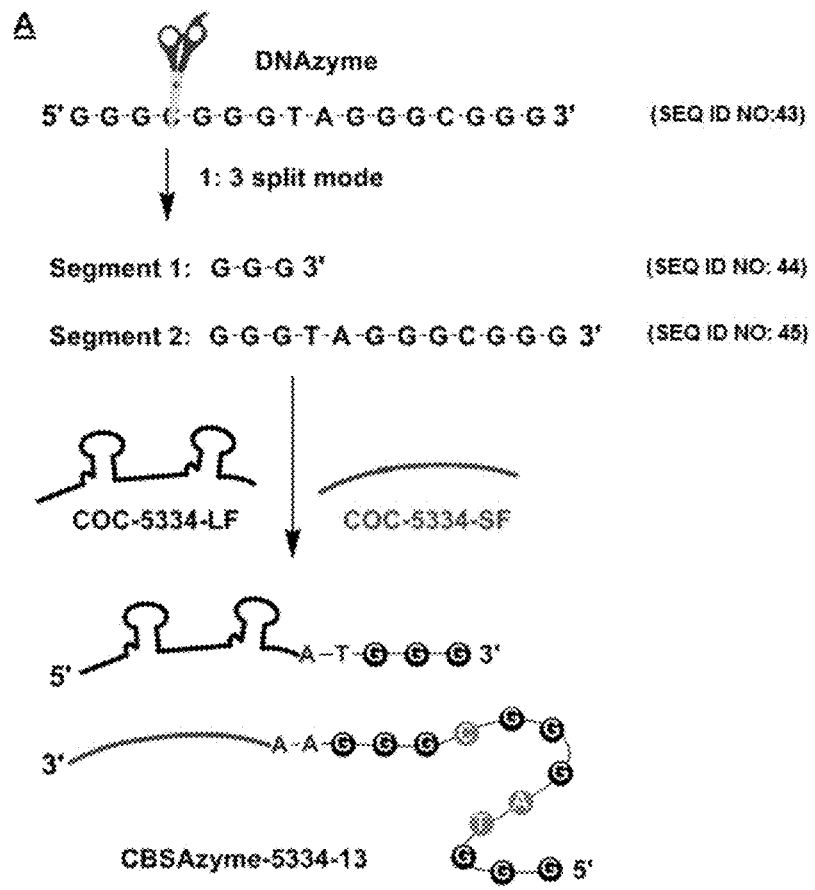

A large background signal was observed in the absence of cocaine with CBSAzyme-5334-22. Since further destabilization of the CBSA module decreased the signal gain, the DNAzyme module was destabilized as an alternative means to reduce the background signal. Studies have shown that symmetrically split DNAzymes can more easily self-assemble than those that are asymmetrically split. The DNAzyme was therefore split in a 1:3 mode, with one segment having three GGG repeats and the other only having one, and joined these fragments to the CBSA. Specifically, the three-repeat segment was coupled to the short fragment of the CBSA (COC-5334-SF), and the single-repeat segment was coupled onto the long fragment (COC-5334-LF), thereby generating CBSAzyme-5334-13 (FIG. 6A).

Figure 6B:
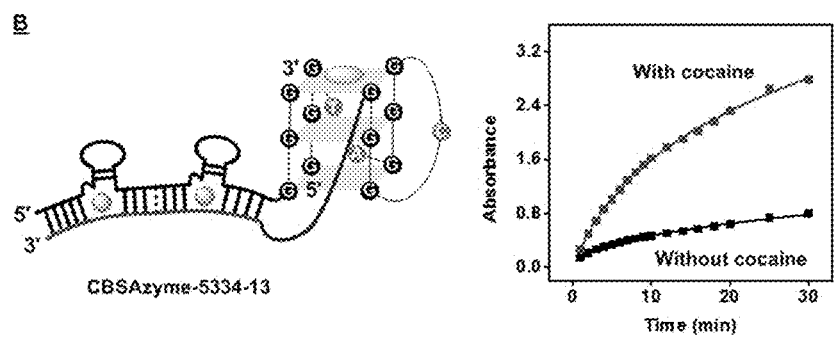

The performances of CBSAzyme-5334-13 and CBSAzyme-5334-22 were compared in the absence and presence of 250 µM cocaine, and different levels of activity and background were observed (FIGS. 6B and C). CBSAzyme-5334-13 demonstrated much lower background assembly relative to CBSAzyme-5334-22 in the absence of cocaine, most likely due to the low stability of 1:3 split DNAzymes. The 1:3 split CBSAzyme also had a higher level of activity in the presence of cocaine relative to the 2:2 split CBSAzyme. The Michaelis-Menten constant (K) and turnover number ($k_{cat}$) were further determined for both CBSAzymes. In the absence of cocaine, CBSAzyme-5334-22 had a slightly lower $K_M$ and higher $k_{cat}$ than the 1:3 split CBSAzyme, which explains its higher background signal. In the presence of cocaine, CBSAzyme-5334-13 had a much lower $K_M$ and higher $k_{cat}$ than the 2:2 split CBSAzyme (FIGS. 7A and B), consistent with the observed higher catalytic activity.

Figure 8:
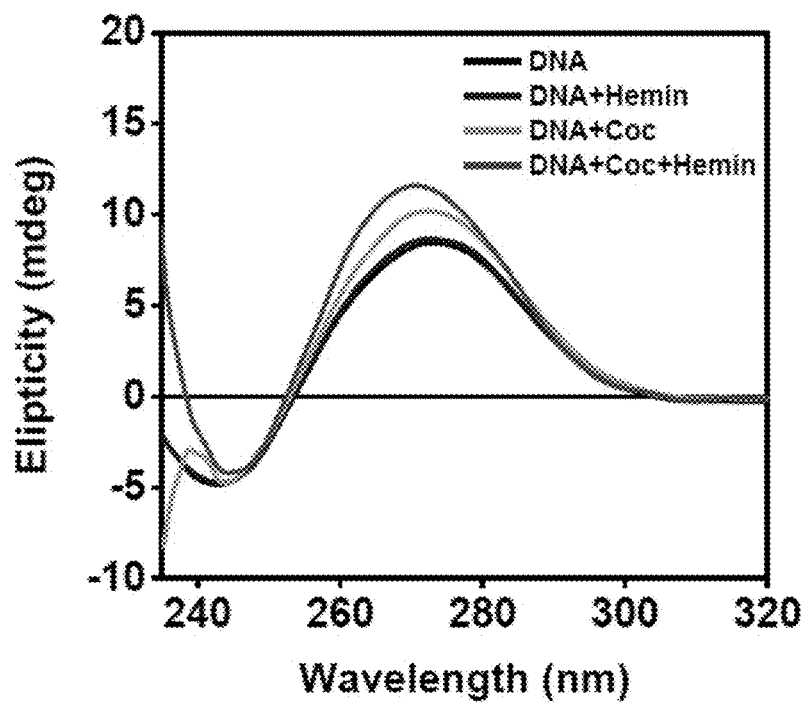
FIG. 8 shows the circular dichroism spectra of 1 μM CBSAzyme-5334-13 alone as well as with 250 μM cocaine, 1 μM hemin, or both. Circular dichroism contributions from cocaine and hemin were subtracted. Buffer conditions: 40 mM HEPES (pH 7.0), 2 mM KCl, 28 mM NaCl, 1% (v/v) DMSO.

The target-induced conformational change of CBSAzyme-5334-13 was then characterized using circular dichroism (FIG. 8). In the presence of only the CBSAzyme, two distinct peaks: a negative peak at 245 nm and a broad positive peak spanning from approximately 260 to 280 nm were observed. The broad positive peak possibly encompasses two merged peaks, wherein one peak at 260 nm arises from a parallel G-quadruplex structure and another at approximately 270 nm originates from a duplex DNA structure. Furthermore, both the G-quadruplex and duplex DNA structures may contribute to the presence of the negative peak at 245 nm. When 1 µM hemin was added, no measurable change occurred in the shape or size of these peaks, indicating that hemin itself cannot induce assembly of the CBSA or DNAzyme. The ellipticity increased at 270 nm when only cocaine was added, demonstrating target-induced CBSA assembly. Further addition of hemin induced a peak shift from 270 to 265 nm with an accompanying increase in the ellipticity of the peak, which likely corresponded to full assembly of the CBSA and DNAzyme modules. This shows that although cocaine can assemble both CBSA fragments, hemin is required for split DNAzyme assembly.

Figure 9:
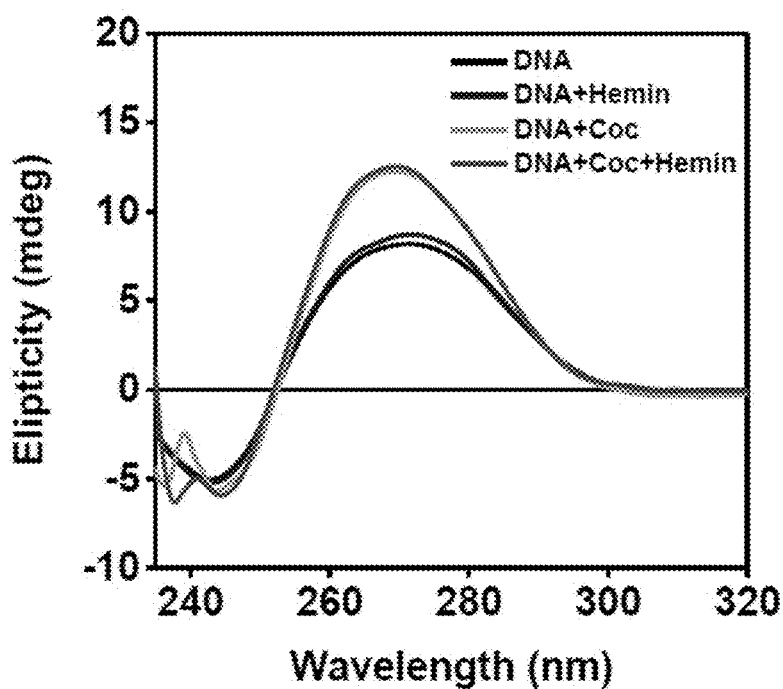
FIG. 9 shows the circular dichroism spectra of 1 μM CBSAzyme-5334-22 alone as well as with 250 μM cocaine, 1 μM hemin, or both. Circular dichroism contributions from cocaine and hemin were subtracted. Buffer conditions: 40 mM HEPES (pH 7.0), 7 mM KCl, 7 mM NaCl, 1% DMSO.

As a control, the conformational changes of CBSAzyme-5334-22 were monitored (FIG. 9). The circular dichroism spectrum for this CBSAzyme resembled that of CBSAzyme-5334-13. Hemin alone again induced no observable change in the size or shape of the spectra. In the presence of cocaine alone, the ellipticity of the peaks at 263 nm and 270 nm notably increased, but the subsequent addition of hemin did not cause any meaningful further change in the spectra. These results indicate that the split DNAzyme segments can readily assemble even without hemin, supporting the notion that the 2:2 split DNAzyme has a strong tendency to self-assemble. This likely explains the large improvement in background signal observed when using the 1:3 split mode.

Example 5—Optimization of the CBSAzyme Linker

To further optimize the signal gain produced by the CBSAzyme, the impact of the linker length between the CBSA and DNAzyme modules on target-induced assembly and catalytic response was investigated. A variant of the long fragment of CBSAzyme-5334-13 was first synthesized, in which the linker was shortened from AT to A and the assay with the corresponding short fragment was then performed in the presence and absence of 250 µM cocaine.

Figures 10A, 10B, 10C:
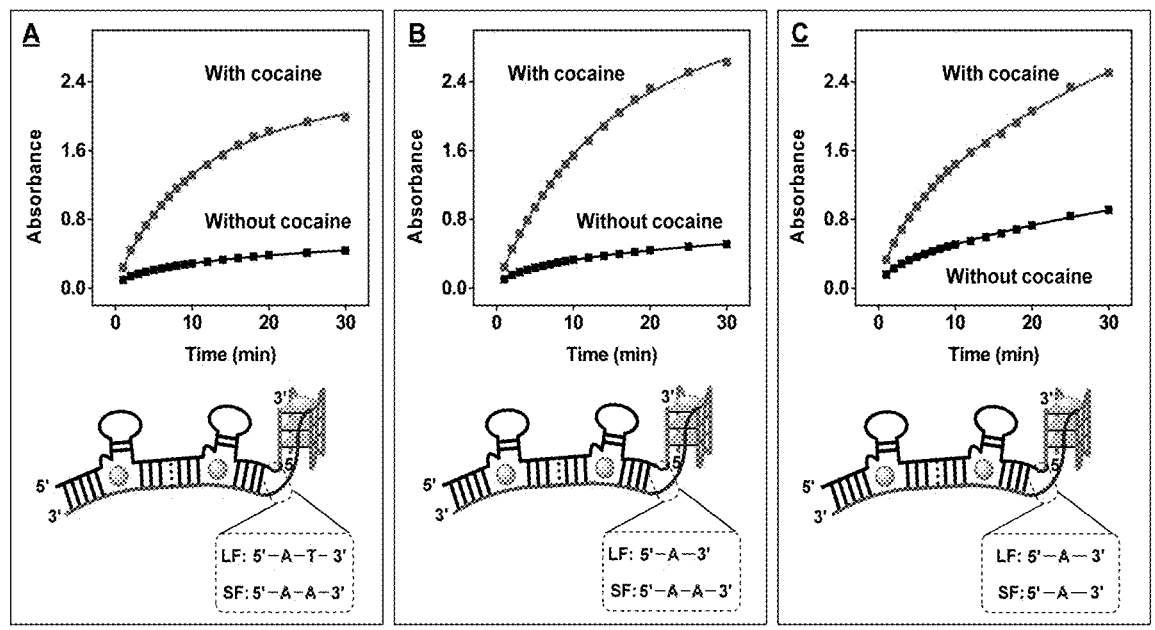
FIGS. 10A-10C show the optimization of the linker of CBSAzyme-5334-13. Structure and time-course of CBSAzyme-5334-13 with linkers comprising (10A) AT/AA (LF: SEQ ID NO: 18; SF: SEQ ID NO: 19), (10B) A/AA (LF: SEQ ID NO: 20; SF: SEQ ID NO: 19), and (10C) A/A (LF: SEQ ID NO: 20; SF: SEQ ID NO: 21) in the absence and presence of 250 μM cocaine. The absorbance at 418 nm was recorded over 30 minutes. [Each fragment]=1 μM.
Figure 11:
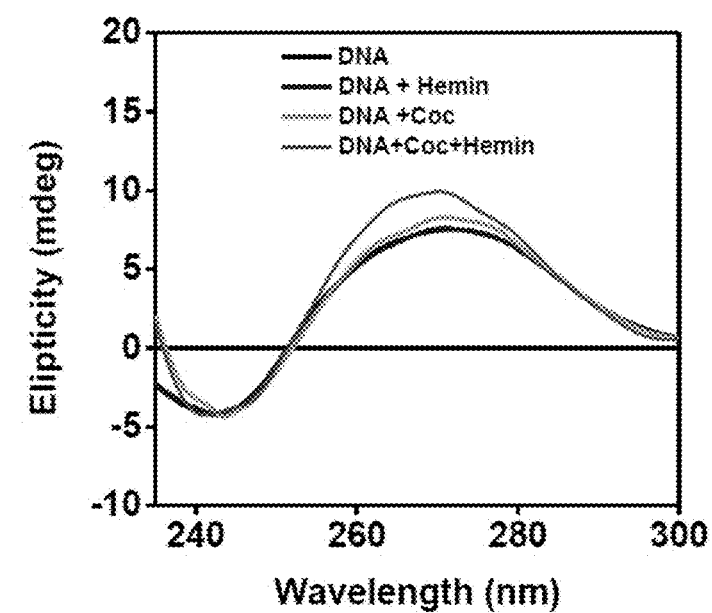
FIG. 11 shows the circular dichroism spectra of 1 μM COC-CBSAzyme (LF: SEQ ID NO: 20; SF: SEQ ID NO: 19) alone as well as with 250 μM cocaine, 1 μM hemin, or both. Circular dichroism contributions from cocaine and hemin were subtracted. Buffer conditions: 40 mM HEPES (pH 7.0), 1 mM KCl, 30 mM NaCl, 1% DMSO.

In comparison to the original construct, which achieved a cocaine-induced signal gain of 4.50 (FIG. 10A), shortening the linker of the long fragment yielded improved CBSAzyme performance, with a signal gain of 5.27 (FIG. 10B). The linker of the short fragment of CBSAzyme-5334-13 was then modified by replacing the original AA linker with a single A, and this variant's performance was tested in conjunction with the optimized long fragment. Shortening this linker had deleterious effects on DNAzyme performance (signal gain=2.83) (FIG. 10C), and the original linker of the short fragment (AA) was therefore retained. The optimized A/AA linker combination favors assembly of both the CBSA and the split DNAzyme. Circular dichroism analysis of the assembled split DNAzyme confirmed that it retained a parallel G-quadruplex structure in the presence of hemin and cocaine (FIG. 11), corresponding to its high DNAzyme activity.

Example 6—Colorimetric Detection of Cocaine with the CBSAzyme

Figures 12A, 12B, 12C:
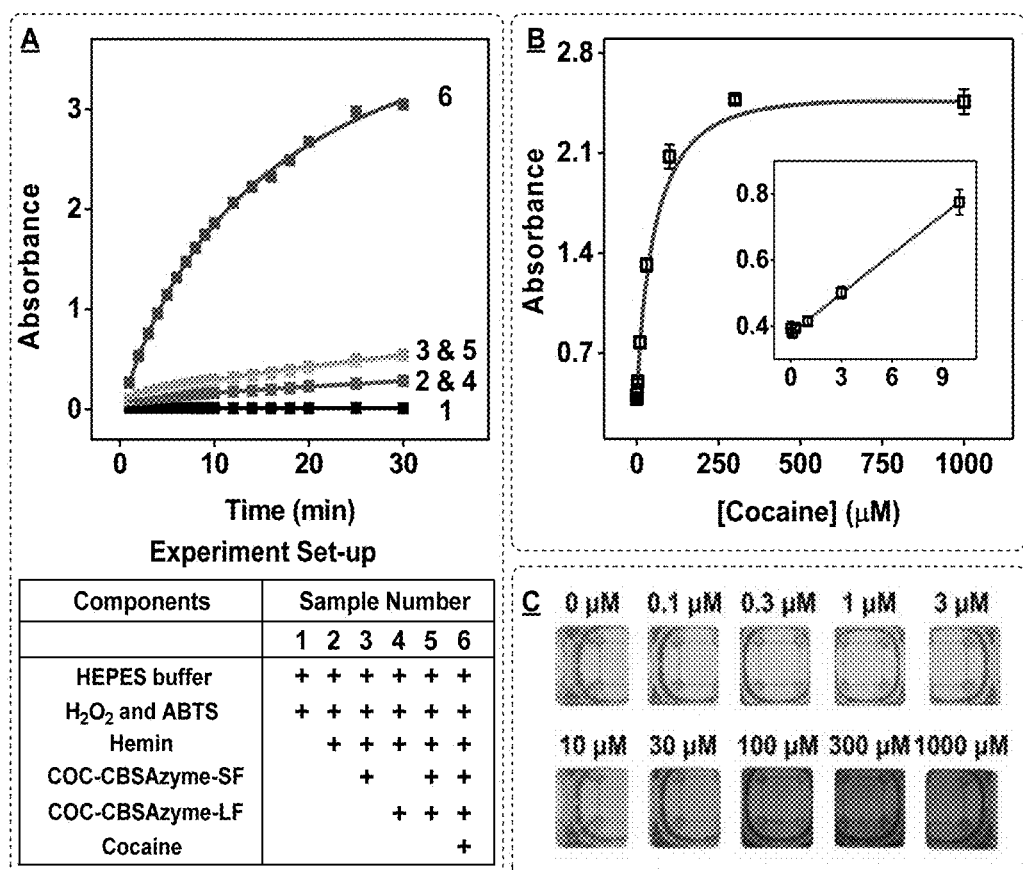
FIGS. 12A-12C show utilizing COC-CBSAzyme for the visual detection of cocaine. (12A) Time-dependent absorbance change at 418 nm with (1) reaction buffer alone, (2) hemin alone, (3) short fragment with hemin, (4) long fragment with hemin, and both fragments plus hemin in the (5) absence or (6) presence of cocaine. (12B) Calibration curve generated using 0-1,000 μM cocaine. Inset represents linear range from 0 to 10 μM cocaine. (12C) Photographs of samples containing 0-1,000 μM cocaine after 15 minutes of reaction. [Each fragment]=1 μM.
Figure 13:
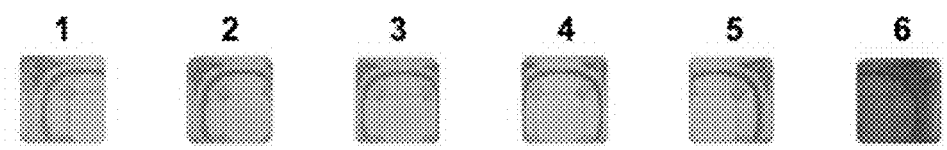
FIG. 13 shows utilizing COC-CBSAzyme for the naked-eye detection of cocaine. Experimental setup shows sample contents and photographs depict the color of the samples containing (1) reaction buffer alone, (2) 1 μM hemin alone, (3) 1 μM short fragment with hemin, (4) 1 μM long fragment with hemin, and both fragments plus hemin in the (5) absence and (6) presence of 250 μM cocaine after 15 minutes of reaction.
Figures 14A, 14B:
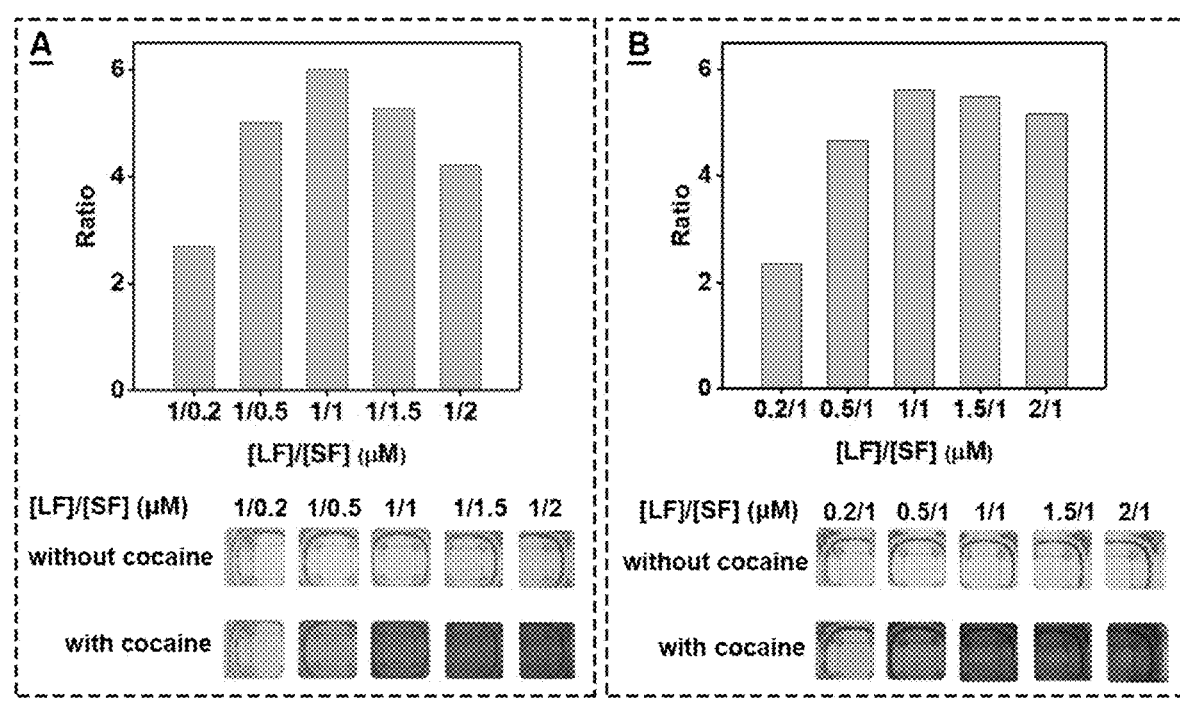
FIGS. 14A-14B show the optimization of the concentrations of the long and short fragments of COC-CBSAzyme in the CBSAzyme-based colorimetric assay. The assay was performed in the presence and absence of 250 μM cocaine with (14A) 1 μM long fragment and 0.2, 0.5 1, 1.5 or 2 μM of short fragment, or (14B) 0.2, 0.5 1, 1.5 or 2 μM long fragment and 1 μM of short fragment. Top panels show the signal gain obtained with various ratios of long and short fragment after 15 minutes of reaction. Bottom panels are photographs depicting the color of the samples.

The optimized construct, termed COC-CBSAzyme, was employed for the visual detection of cocaine. A series of control experiments verified that signal is only obtained in the presence of cocaine (FIG. 12A). No signal was observed with $H_2O_2$ and ABTS alone; when hemin was added, ABTS was slowly oxidized by $H_2O_2$ to produce a minor increase in absorbance at 418 nm. Further addition of the long fragment did not produce any signal change, but addition of the short fragment with hemin in the absence of long fragment produced low levels of background. This is probably because the short fragment contains three guanine triplets, which may form intra- or intermolecular G-quadruplexes that can accommodate hemin to catalyze the oxidation of ABTS. When both fragments were included in the same mixture without target, low levels of background signal identical to that obtained with the short fragment alone were observed, indicating that the fragments only underwent minimal assembly in the absence of target. The addition of 250 µM cocaine promoted assembly of the split DNAzyme, yielding a large change in absorbance (FIG. 12A) and rapid development of a dark green color within 15 minutes (FIG. 13). To determine the optimum concentrations of short and long fragment, the COC-CBSAzyme-based assay was performed with varying concentrations of short fragment (0.2 to 2 µM) while keeping the concentration of the long fragment at 1 µM and vice versa. The results show that 1 µM of each fragment produces the highest signal gain (FIG. 14).

Figure 15:
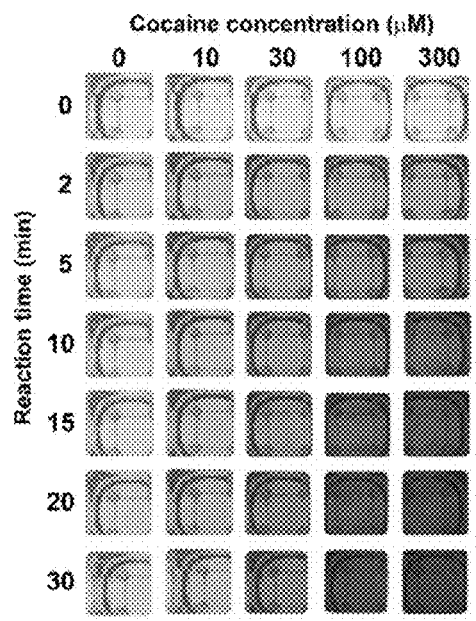
FIG. 15 shows the time-course visual detection of cocaine using COC-CBSAzyme (LF: SEQ ID NO: 20; SF: SEQ ID NO: 19). Photographs of the samples containing different concentrations of cocaine (0-300 μM) at different time points (0-30 min) are shown. The color of the cocaine-containing samples progressively changes over time, while the color of the cocaine-free sample only changed slightly.

The performance of the assay was then determined for the visual detection of cocaine. In the absence of cocaine, the color of the solution did not change, even after 30 minutes of reaction. However, in the presence of cocaine, the absorbance of $ABTS^{\bullet+}$ gradually increased and the solution became green over time (FIG. 15). Cocaine at concentrations as low as 10 µM was detected with the naked eye within only 5 minutes, and the color intensity of the solution was proportional to the concentration of cocaine (FIG. 15). A microplate reader was used to generate a calibration curve using the absorbance of $ABTS^{\bullet+}$ at 418 nm after 15 minutes of reaction and obtained a measurable limit of detection of 1 µM with a linear range of 0 to 100 µM (FIGS. 12B and C).

Figure 16A:
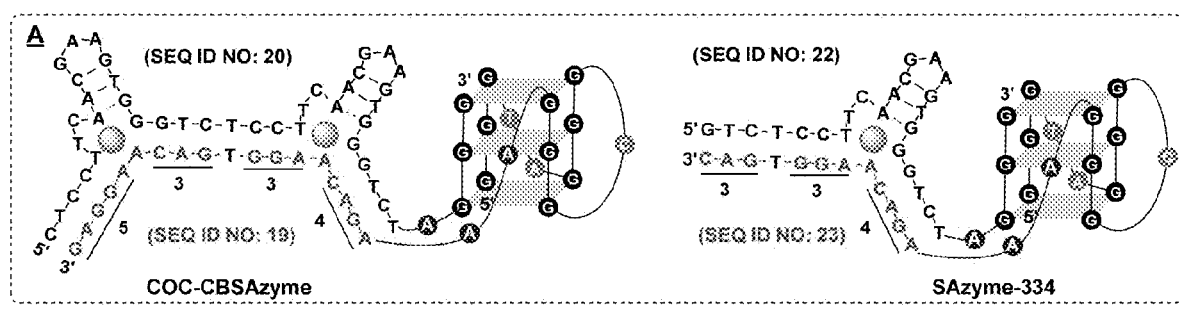

The performance of the CBSAzyme was compared to a DNAzyme-linked split aptamer with a single binding site. This variant was synthesized by truncating the 5-bp double-stranded duplex and the adjacent binding site from the 5' end of the long fragment of COC-CBSAzyme to form SAzyme-334 (FIG. 16A). Whereas a clear color change was observed with COC-CBSAzyme at cocaine concentrations as low as 10 µM after only 2 minutes, a color change with SAzyme-334 was not observed at cocaine concentrations lower than 300 µM, even after 15 minutes (FIG. 16B). This demonstrates the far lower target responsiveness of the single-site SAzyme-334 construct relative to the COC-CBSAzyme.

The specificity of the assay was further tested against 250 µM concentrations of various interferent drugs, including chlorpromazine, diphenhydramine, promazine, and scopolamine, as well as common cutting agents found in street samples such as caffeine, levamisole, lidocaine, and sucrose (FIG. 17A). No cross-reactivity to scopolamine and sucrose, and minimal cross-reactivity to caffeine, chlorpromazine, promazine, and levamisole at this concentration was observed. However, moderate cross-reactivity was observed for diphenhydramine and lidocaine (FIGS. 17B and C). This was expected, given that the cocaine-binding aptamer has previously-reported cross-reactivity to these molecules.

Example 7—Demonstrating Generality of the CBSAzyme Assay Format for Detection of MDPV MDPV is a member of the family of designer drugs known as synthetic cathinones—a class of drugs for which assay development lags well behind the emergence of new molecules into the market. An MDPV-binding CBSA was generated based on an isolated three-way-junction-structured DNA aptamer (FIG. 18A, I) that binds to MDPV with a $K_D$ of 6 µM. Specifically, two different parent split aptamer pairs (FIG. 18A, II) was derived with a single binding pocket from the MDPV-binding aptamer, in which the GAA loop from stem 3 was removed and the number of base-pairs in all stems was decreased. Stem 1 of one parent split aptamer was then connected to stem 3 of the second via a single thymine linker on each strand to form a MDPV-binding CBSA, MDPV-6335 (FIG. 18A, III).

To determine the binding affinity and cooperativity of MDPV-6335, the short fragment was modified with a 5' IowaBlack RQ quencher and a 3' Cy5 fluorophore (FIG. 18B). In the absence of MDPV, the two fragments remain separate, with the fluorophore-quencher pair of the short fragment remaining in close proximity to each other and thus yielding no fluorescence signal (FIG. 18B, left). When the target is added, the CBSA assembles to form a rigid target-CBSA complex, separating the fluorophore-quencher pair and producing a large fluorescence signal (FIG. 18B, right). This fluorophore-quencher-modified version of MDPV-6335 was used to generate a binding curve for MDPV concentrations ranging from 0-3,000 µM, and the resulting curve was fitted with the Hill equation (FIG. 18C). MDPV-6335 had a binding affinity ($K_{1/2}$, target concentration producing half occupancy) of 140.6 µM with a cooperativity ($n_H$) of 1.8, which shows the high degree of target binding cooperativity.

Figures 19A, 19B:
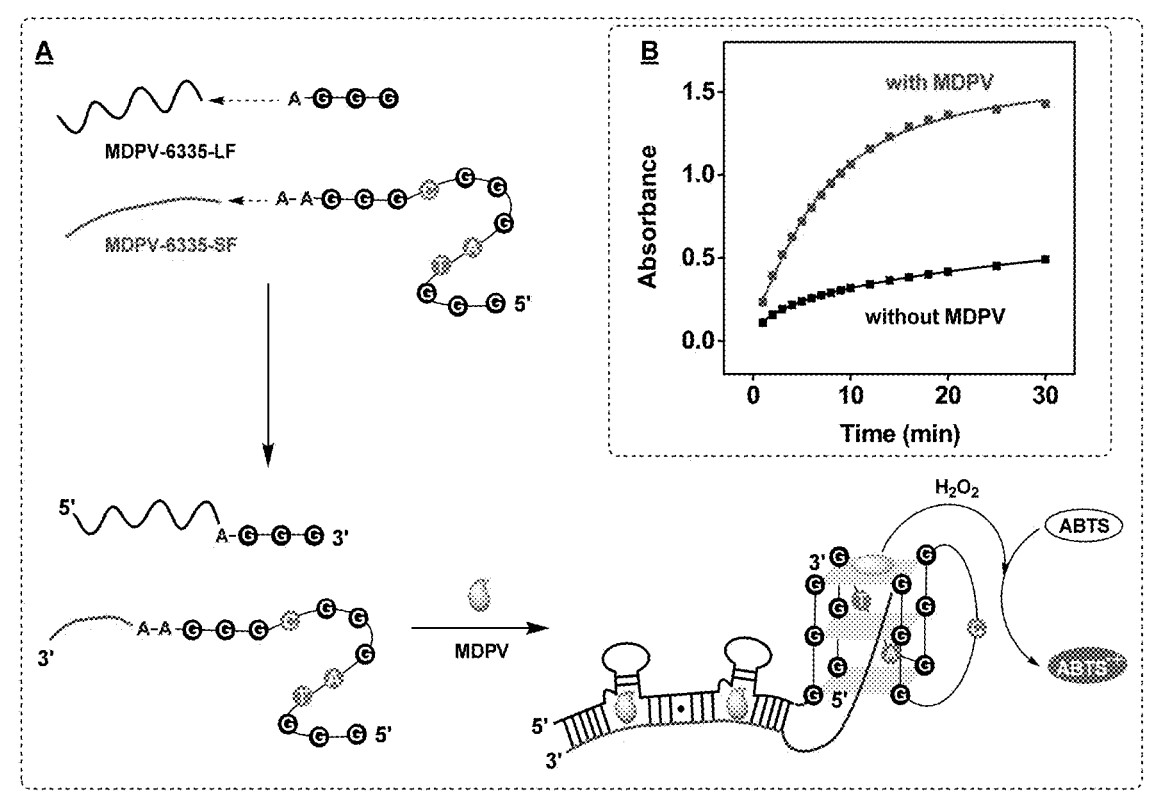
Figure 20:
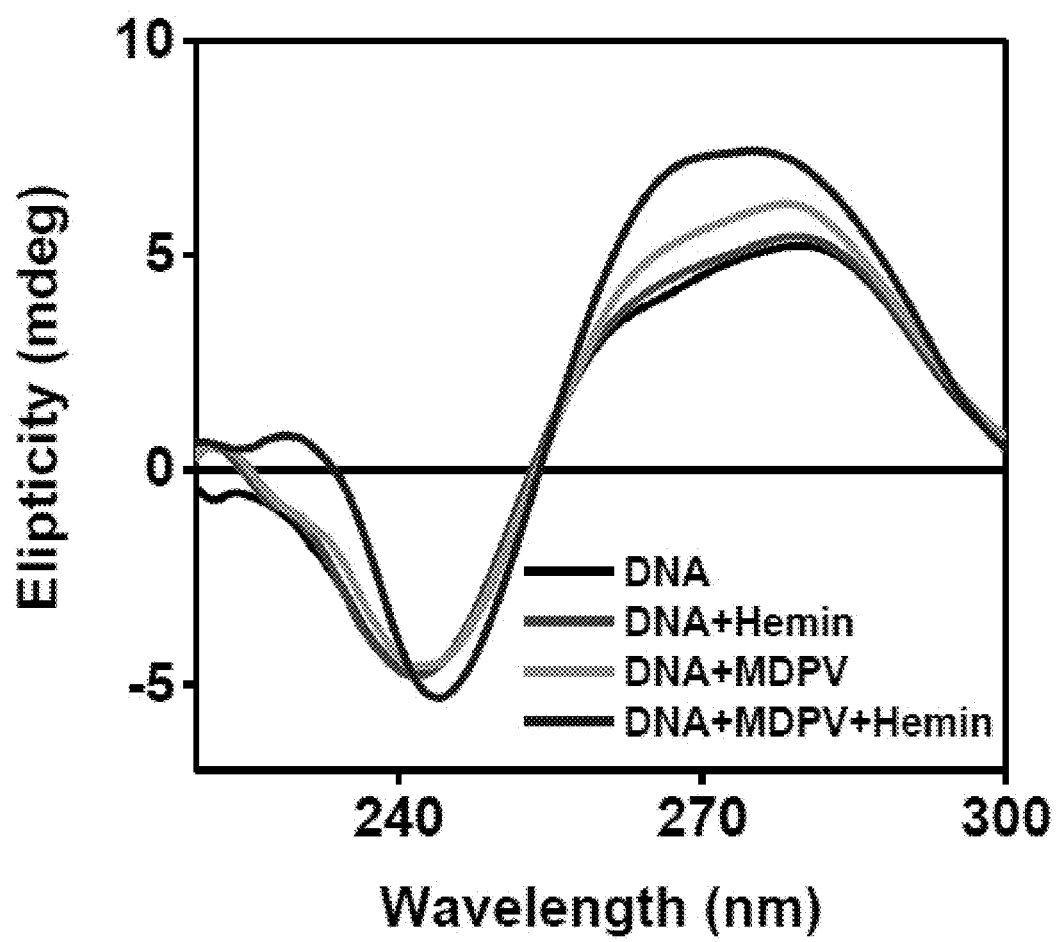
FIG. 20 shows the circular dichroism spectra of 1 µM MDPV-CBSAzyme (LF: SEQ ID NO: 28; SF: SEQ ID NO: 29) alone and with 200 µM MDPV, 1 µM hemin, or both. Circular dichroism contributions from MDPV and hemin were subtracted. Buffer conditions: 40 mM HEPES pH 7, 7 mM KCl, 77 mM NaCl, 1% DMSO.

A MDPV-binding CBSAzyme was then generated by incorporating the optimized DNAzyme and linker sequences described above into the short and long fragments of MDPV-6335 to form MDPV-CBSAzyme (FIG. 19A). The performance of this CBSAzyme was tested and a high signal gain was obtained in the presence of MDPV after 15 minutes (FIG. 19B). Circular dichroism was also used to confirm the structure and target-induced conformational changes of MDPV-CBSAzyme (FIG. 20). For the CBSAzyme alone, two peaks were observed: a negative peak at 241 nm and a broad positive peak with a maximum at 275 nm and a shoulder at 260 nm. The peaks at 260 nm and 275 nm correspond to background assembly of the G-quadruplex-structured DNAzyme and duplex-structured CBSA, respectively, while the peak at 241 nm represents assembly of both modules. With the addition of hemin, the spectra did not change, indicating that hemin was unable to assemble either the CBSA or the split DNAzyme. With the addition of MDPV alone, a slight increase was observed in the 275 nm positive peak, indicating low levels of target-induced CBSA assembly. When both hemin and MDPV were added, the positive peaks at 260 nm and 275 nm increased, confirming that both hemin and MDPV are required for efficient assembly.

Figure 22:
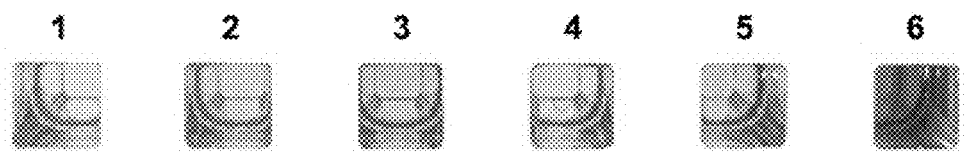
FIG. 22 shows utilizing MDPV-CBSAzyme for the naked-eye detection of MDPV. Experimental setup shows sample contents and photographs depict the color of the samples containing (1) reaction buffer alone, (2) 1 µM hemin alone, (3) 1 µM short fragment with hemin, (4) 1 µM long fragment with hemin, and both fragments plus hemin in the (5) absence or (6) presence of 250 µM MDPV after 15 minutes of reaction.
Figure 23:
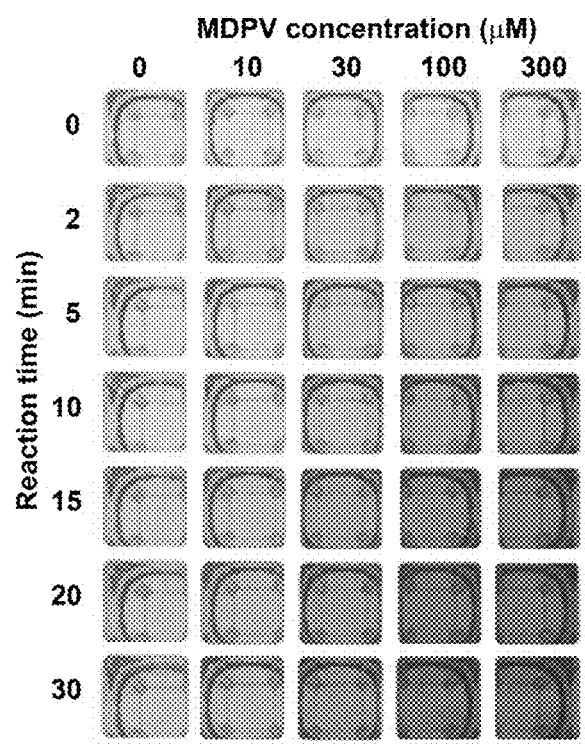
FIG. 23 shows the time-course visual detection of MDPV using MDPV-CBSAzyme. Photographs of the samples containing different concentrations of MDPV (0-300 µM) at different time points (0-30 min) are shown. The color of the MDPV-containing samples progressively changes over time, while the color of the cocaine-free sample only changed slightly.

This MDPV-CBSAzyme was used for visual detection of MDPV. Control experiments confirmed that the CBSAzyme only produces a target-related signal (FIGS. 21A and 22). No background signal was observed with the reaction buffer and hemin, or with the long fragment and hemin. As with the cocaine assay, a very small absorbance signal was observed with the mixture of short fragment and hemin, probably due to the fact that its three guanine triplets form inter- or intramolecular G-quadruplexes that can accommodate hemin to facilitate ABTS oxidation. Similar low levels of absorbance signal was observed when both long and short fragments were combined with hemin in the absence of target, but no visible color change in the solution occurred even after 30 minutes of reaction. When MDPV was added, the absorbance of ABTS$^{•+}$ gradually increased (FIG. 21A) and the solution rapidly developed a dark green color over 15 minutes (FIG. 22). A calibration curve was then generated using the absorbance ABTS$^{•+}$ at 418 nm after 15 minutes and obtained a detection limit of 3 µM MDPV with a linear range from 0 to 100 µM (FIGS. 21B and C). Importantly, MDPV concentrations as low as 30 µM were able to be detected by naked eye within 5 minutes (FIG. 23).

Figures 24A, 24B:
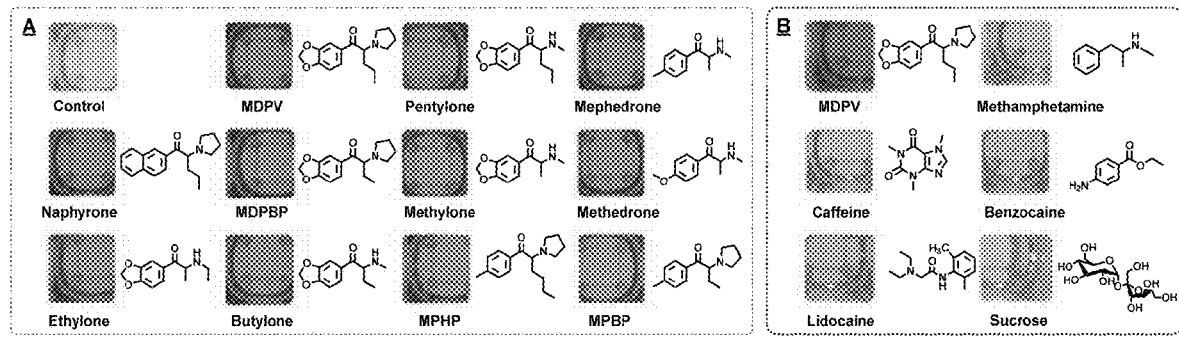
FIGS. 24A-24B show the cross-reactivity and specificity of the colorimetric MDPV-CBSAzyme-based assay. Photographs of samples containing (24A) buffer-only control sample, 11 synthetic cathinones and (24B) MDPV or 5 interferents after 15 minutes of reaction. All drugs or interferents were present at 250 µM. [Each fragment]=1 µM.
Figure 25:
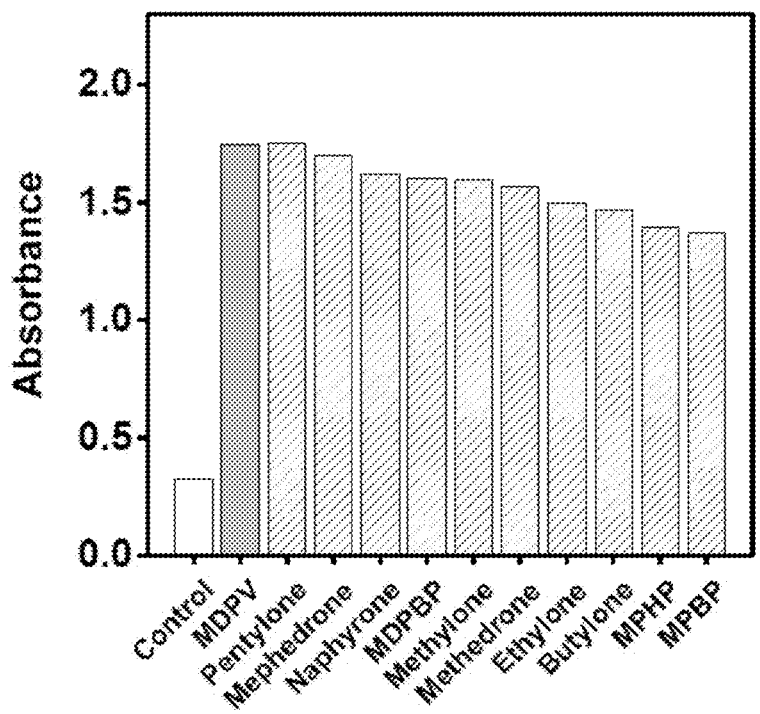
FIG. 25 shows the target-cross-reactivity of the MDPV-CBSAzyme-based assay. Absorbance of samples at 418 nm after 15 minutes for samples containing 11 different synthetic cathinones at a concentration of 250 µM is shown.
Figure 26:
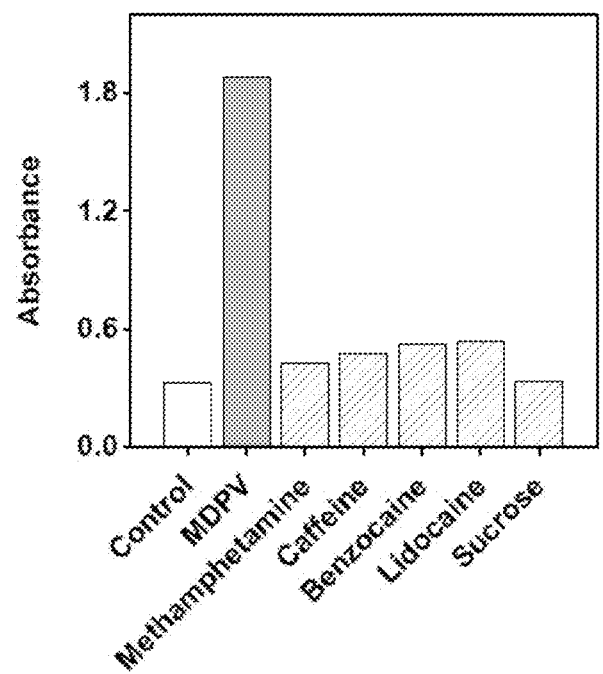
FIG. 26 shows the specificity of the MDPV-CBSAzyme-based assay. Absorbance of samples at 418 nm after 15 minutes for samples containing various interferents (250 µM) is shown. MDPV is used as a positive control.

The MDPV-CBSAzyme can be used to visually detect a variety of synthetic cathinones. Specifically, The CBSAzyme-based assay was challenged against 250 µM concentrations of 11 different synthetic cathinones, including MDPV, methylone, pentylone, 3,4-methylenedioxy-α-pyrrolidinobutiophenone (MDPBP), mephedrone, 4-methyl-α-pyrrolidinobutiophenone (MPBP), 4'-methyl-α-pyrrolidinohexanophenone (MPHP), naphyrone, methedrone, ethylone, and butylone. As expected, a dark green color (FIG. 24A) and a high signal gain (FIG. 25) were observed after 15 minutes for all tested synthetic cathinones, indicating that MDPV-CBSAzyme retains excellent cross-reactivity to structurally-similar synthetic cathinone analogs. In addition, the CBSAzyme-based assay retained excellent specificity against interferents, as no measurable signal was observed with 250 µM concentrations of common cutting agents and illicit drugs such as caffeine, benzocaine, lidocaine, sucrose and methamphetamine (FIGS. 24B and 26). Based on the success of CBSAzyme-based assays for colorimetric cocaine and MDPV detection, this assay can be generalized to detect any small molecule in a simple, label- and instrument-free manner.

Figure 27:
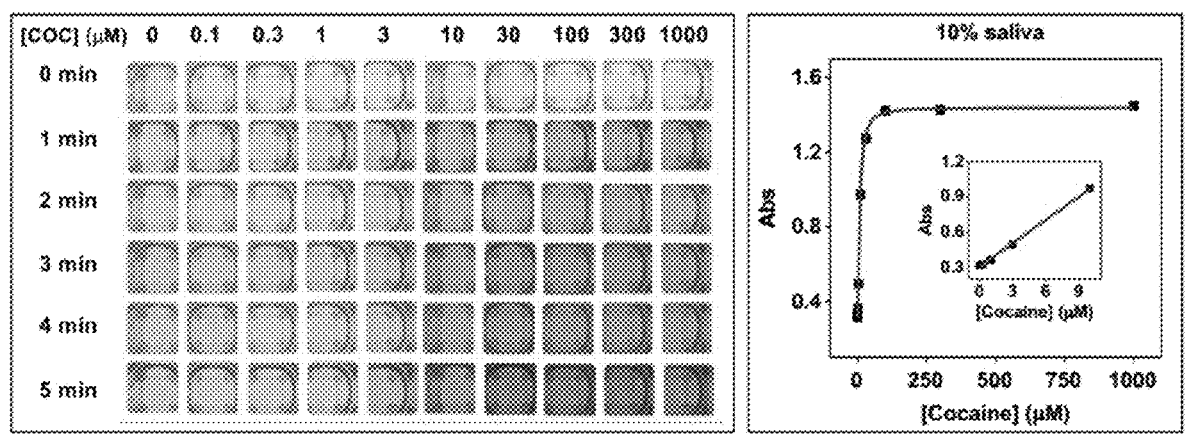
FIG. 27 shows the time-course for visual detection of cocaine in 10% saliva using COC-CBSAzyme (LF: SEQ ID NO: 20; SF: SEQ ID NO: 19). (left) Photographs of the samples containing different concentrations of cocaine (COC) (0-1000 µM) at different time points (0-5 min) are shown. The color of the cocaine-containing samples progressively changes over time, while the color of the cocaine-free sample only changed slightly. (right) Calibration curve generated using 0-1000 µM cocaine after 5 minutes of reaction. The limit of visual detection is 3 µM cocaine.
Figure 28:
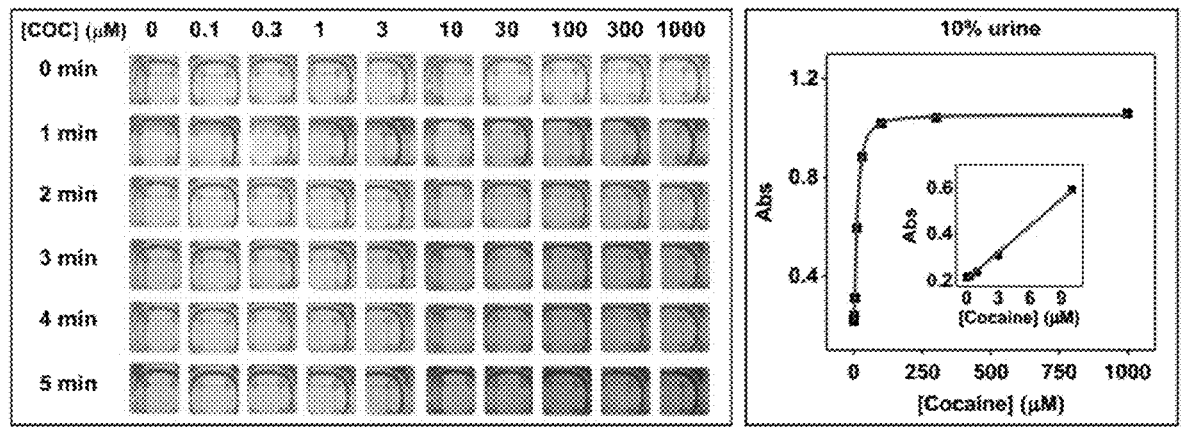
FIG. 28 shows the time-course visual detection of cocaine in 10% urine using COC-CBSAzyme (LF: SEQ ID NO: 20; SF: SEQ ID NO: 19). (left) Photographs of the samples containing different concentrations of cocaine (COC) (0-1000 µM) in at different time points (0-5 min) are shown. The color of the cocaine-containing samples progressively changes over time, while the color of the cocaine-free sample only changed slightly. (right) Calibration curve generated using 0-1000 µM cocaine after 5 minutes of reaction. The limit of visual detection is 3 µM cocaine.

Example 8—Detecting Cocaine and MDPV in Biological Samples Using the CBSAzyme-Based Sensor To demonstrate the visual detection of cocaine in a biological sample, COC-CBSAzyme (LF: SEQ ID NO: 20; SF: SEQ ID NO: 19) was used to detect cocaine at different concentrations of cocaine (COC) (0-1000 µM) in 10% saliva (FIG. 27) and 10% urine (FIG. 28) samples, respectively. The color of the cocaine-containing samples progressively changes over time, while the color of the cocaine-free sample only changed slightly (FIGS. 27 left and 28 left). Cocaine at concentrations of 10 µM and higher can be detected within one minute. A calibration curve was generated using 0-1000 µM cocaine after five minutes of reaction in 10% saliva (FIG. 27 right) and 10% urine (FIG. 28 right). The limit of visual detection is 3 µM cocaine.

Figure 29:
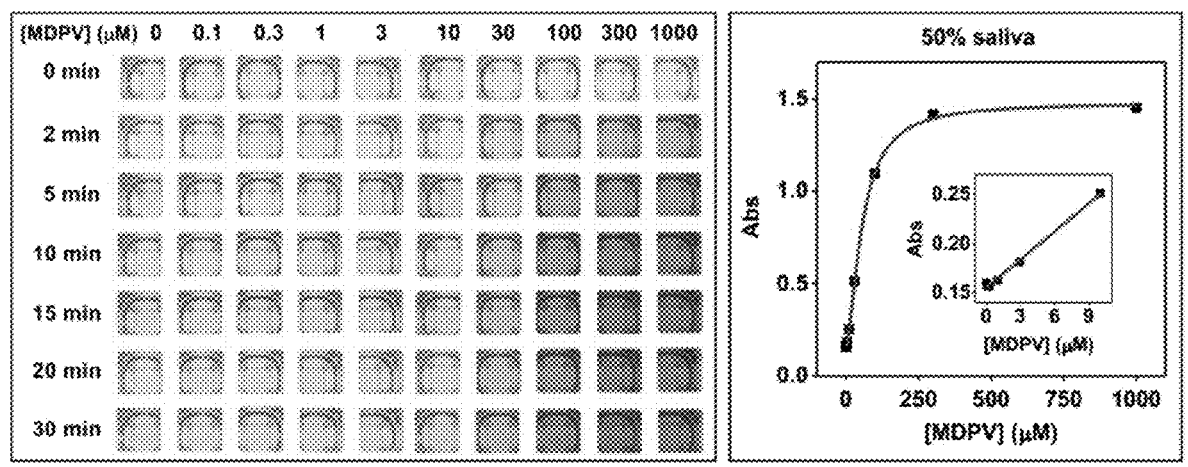
FIG. 29 shows the time-course visual detection of MDPV in 50% saliva using MDPV-CBSAzyme (LF: SEQ ID NO: 28; SF: SEQ ID NO: 29). (left) Photographs of the samples containing different concentrations of MDPV (0-1000 µM) at different time points (0-30 min) are shown. The color of the MDPV-containing samples progressively changes over time, while the color of the MDPV-free sample only changed slightly. (right) Calibration curve generated using 0-1000 µM MDPV after 15 minutes of reaction. The limit of visual detection is 30 µM MDPV.
Figure 30:
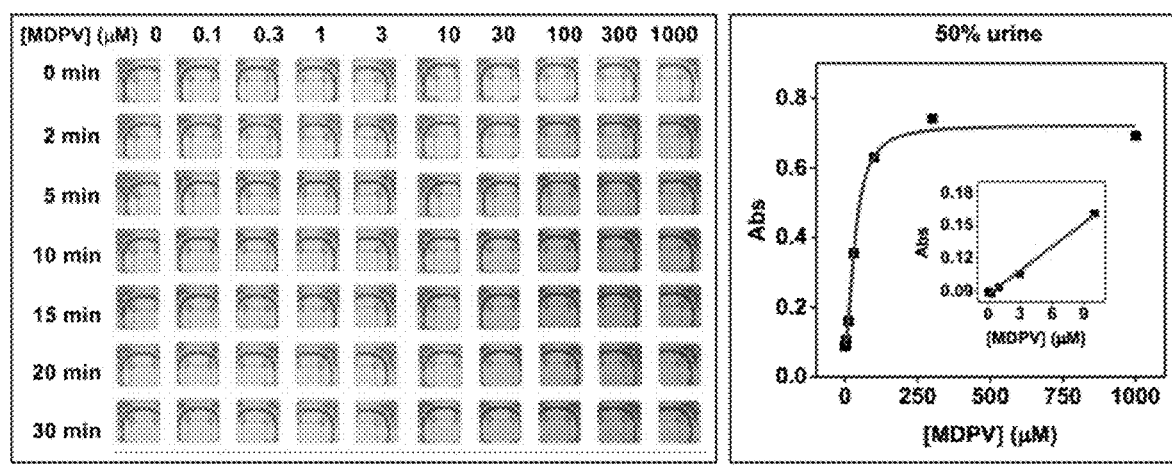
FIG. 30 shows the time-course visual detection of MDPV in 50% urine using MDPV-CBSAzyme (LF: SEQ ID NO: 28; SF: SEQ ID NO: 29). (left) Photographs of the samples containing different concentrations of MDPV (0-1000 µM) at different time points (0-30 min) are shown. The color of the MDPV-containing samples progressively changes over time, while the color of the MDPV-free sample only changed slightly. (right) Calibration curve generated using 0-1,000 µM MDPV after 15 minutes of reaction. The limit of visual detection is 30 µM MDPV.

To demonstrate the visual detection of MDPV in a biological sample, MDPV-CBSAzyme (LF: SEQ ID NO: 28; SF: SEQ ID NO: 29) was used to detect MDPV at different concentrations of MDPV (0-1000 µM) in 50% saliva (FIG. 29) and 50% urine (FIG. 30) samples, respectively. The color of the MDPV-containing samples progressively changes over time, while the color of the MDPV-free samples shows no obvious changes (FIGS. 29 left and 30 left). MDPV at concentrations of 30 µM and higher can be detected within five minute in both 50% saliva and 50% urine samples. A calibration curve was generated using 0-1000 µM MDPV after 15 minutes of reaction in 50% saliva (FIG. 29 right) and 50% urine (FIG. 30 right). The limit of visual detection is 30 µM MDPV.

What is claimed is:

1. A cooperative binding split aptamer (CBSA)-DNAzyme conjugate (CBSAzyme) comprising a first fragment and a second fragment, the first fragment comprising a first segment of a split DNAzyme and a long fragment of a CBSA, and the second fragment comprising a second segment of the split DNAzyme and a short fragment of the CBSA, the first and second segments of the split DNAzyme being split from a DNAzyme having a G-quadruplex-structure and peroxidase activity, two fragments of CBSAzyme assembling upon binding of a target molecule of the CBSA.

2. The CBSAzyme according to claim 1, the long fragment of the CBSA being linked to the first segment of the split DNAzyme via a first linker, and the short fragment of the CBSA being linked to the second segment of the split DNAzyme via a second linker.

3. The CBSAzyme according to claim 2, the first and second linkers being independently selected from A, C, T, AA, AC, AT, CC, CA, CT, TA, TC, and TT.

4. The CBSAzyme according to claim 1, the DNAzyme being split in a 1:3 or 2:2 mode.

5. The CBSAzyme according to claim 1, the DNAzyme having a sequence of SEQ ID NO: 43 or a sequence sharing at least 90% identity thereto.

6. The CBSAzyme according to claim 1, the DNAzyme comprising one or more GGG repeats.

7. The CBSAzyme according to claim 1, the DNAzyme comprising 4 GGG repeats.

8. The CBSAzyme according to claim 1, the first segment of the split DNAzyme comprising one or two GGG repeats, and the second segment of the split DNAzyme comprising two or three GGG repeats.

9. The CBSAzyme according to claim 1, the first and/or second fragment of the split DNAzyme comprising 5'-GXG-GYGGG-3' (SEQ ID NO: 36), wherein X and Y are spacers and can be missing.

10. The CBSAzyme according to claim 9, X and Y being independently selected from A, C, T, AA, AC, AT, CC, CA, CT, TA, TC, and TT.

11. A CBSAzyme-based sensor comprising a CBSAzyme of claim 1 and a signal reporter.

12. The CBSAzyme-based sensor of claim 11, the signal reporter being a mixture of a peroxidase substrate and $H_2O_2$.

13. The CBSAzyme-based sensor of claim 12, the peroxidase substrate being 2, 2'-azinobis(3-ethylbenzthiazoline)-6-sulfonic acid (ABTS) or 3,3',5,5'-Tetramethylbenzidine (TMB).

14. A method for detecting a target molecule in a sample comprising contacting the sample with a CBSAzyme-based sensor of claim 11, and detecting the target molecule in the sample from a signal generated upon binding of the target molecule to the CBSAzyme.

15. The method according to claim 14, the sample being a biological sample or an environmental sample.

16. The method according to claim 14, the signal reporter being a mixture of a peroxidase substrate and $H_2O_2$.

17. The method according to claim 15, the biological sample being selected from urine and saliva.

18. The method according to claim 14, the signal being a change in absorbance or color.

19. The method according to claim 14, the signal being visible to the naked eye.

20. The method according to claim 14, the signal being generated within 5-15 minutes.

* * * * *